United States Patent
O'Connor et al.

(10) Patent No.: US 10,585,993 B2
(45) Date of Patent: Mar. 10, 2020

(54) METHOD AND APPARATUS FOR PERSONALIZED PUTTING OF A GOLF BALL

(71) Applicant: Topcon Positioning Systems, Inc., Livermore, CA (US)

(72) Inventors: Raymond M. O'Connor, Danville, CA (US); Jason Killpack, Portland, OR (US); Kyle Snow, Westerville, OH (US); Justin Tuente, Columbus, OH (US); Chris McKee, Newark, OH (US)

(73) Assignee: Topcon Positioning Systems, Inc., Livermore, CA (US)

( * ) Notice: Subject to any disclaimer, the term of this patent is extended or adjusted under 35 U.S.C. 154(b) by 211 days.

(21) Appl. No.: 15/476,075

(22) Filed: Mar. 31, 2017

(65) Prior Publication Data

US 2018/0285491 A1  Oct. 4, 2018

(51) Int. Cl.
*G06F 17/50* (2006.01)
*A63B 71/06* (2006.01)
*A63B 69/36* (2006.01)
*G16H 20/30* (2018.01)

(52) U.S. Cl.
CPC ...... *G06F 17/5009* (2013.01); *A63B 69/3608* (2013.01); *A63B 69/3685* (2013.01); *A63B 71/0619* (2013.01); *G16H 20/30* (2018.01); *A63B 2071/0658* (2013.01); *A63B 2220/18* (2013.01); *A63B 2225/50* (2013.01)

(58) Field of Classification Search
None
See application file for complete search history.

(56) References Cited

U.S. PATENT DOCUMENTS

| | | | |
|---|---|---|---|
| 4,758,000 | A | 7/1988 | Cox |
| 5,589,628 | A | 12/1996 | Braly |
| 5,707,297 | A | 1/1998 | Shu |
| 6,277,030 | B1 | 8/2001 | Baynton et al. |
| 6,296,579 | B1 | 10/2001 | Robinson |
| 6,457,713 | B1 | 10/2002 | Oppenheimer et al. |
| 6,569,030 | B1 | 5/2003 | Hamilton |

(Continued)

FOREIGN PATENT DOCUMENTS

| | | |
|---|---|---|
| JP | 2002204846 A | 7/2002 |
| WO | 92/22359 A1 | 12/1992 |

(Continued)

OTHER PUBLICATIONS

King Kevin, et al., "Wireless MEMS Inertial Sensor System for Golf Swing Dynamics", Sep. 8, 2007, Sensors and Actuators A 141, Elsevier B.V. (Year: 2007).*

(Continued)

*Primary Examiner* — Cedric Johnson
(74) *Attorney, Agent, or Firm* — Chiesa Shahinian & Giantomasi PC

(57) ABSTRACT

A method and apparatus is provided that determines and simulates the proper putting stroke using at least aiming direction and speed for successfully making a particular putt based on particular putting green characteristics and the location of the golf hole on the putting green, and which is interactive with the user thereby providing an enhanced playing experience and improved putting results.

24 Claims, 20 Drawing Sheets

(56) References Cited

U.S. PATENT DOCUMENTS

| | | | |
|---|---|---|---|
| 7,658,683 B1 | 2/2010 | Daniel | |
| 7,708,658 B2* | 5/2010 | McInerney | A63B 21/153 |
| | | | 473/407 |
| 7,771,284 B1 | 8/2010 | Brown et al. | |
| 7,850,536 B1 | 12/2010 | Fitzgerald | |
| 7,874,929 B2 | 1/2011 | Blanchard et al. | |
| 8,016,689 B2 | 9/2011 | Feys et al. | |
| 8,029,379 B1 | 10/2011 | Johansen | |
| 8,267,812 B1 | 9/2012 | Sery | |
| 8,439,767 B2 | 5/2013 | Feiner | |
| 8,915,792 B2* | 12/2014 | Coucher | A63B 69/3614 |
| | | | 473/220 |
| 2002/0049101 A1 | 4/2002 | Robinson | |
| 2003/0017890 A1 | 1/2003 | McDonald et al. | |
| 2004/0147329 A1 | 7/2004 | Meadows et al. | |
| 2005/0020369 A1* | 1/2005 | Davis | A63B 69/3614 |
| | | | 473/131 |
| 2005/0101415 A1 | 5/2005 | Sweeney | |
| 2005/0227791 A1 | 10/2005 | McCreary et al. | |
| 2006/0166738 A1* | 7/2006 | Eyestone | A63B 15/005 |
| | | | 463/36 |
| 2009/0128503 A1* | 5/2009 | Grant | G06F 3/016 |
| | | | 345/173 |
| 2010/0179005 A1 | 7/2010 | Meadows et al. | |
| 2010/0216565 A1* | 8/2010 | Stites | A63B 69/3614 |
| | | | 473/231 |
| 2012/0276965 A1 | 11/2012 | Ok | |
| 2013/0331195 A1 | 12/2013 | Sery | |
| 2014/0031137 A1 | 1/2014 | Basile | |
| 2014/0065586 A1 | 3/2014 | Gabbai | |
| 2014/0100047 A1 | 4/2014 | Noh et al. | |
| 2014/0180451 A1 | 6/2014 | Marty | |
| 2014/0366650 A1* | 12/2014 | Thillainadarajah | A63B 69/36 |
| | | | 73/862.625 |
| 2015/0019135 A1* | 1/2015 | Kacyvenski | A61B 5/0488 |
| | | | 702/19 |
| 2015/0182825 A1 | 7/2015 | O'Connor et al. | |
| 2016/0045786 A1* | 2/2016 | Cottam | H04M 1/04 |
| | | | 473/409 |
| 2018/0285491 A1 | 10/2018 | O'Connor et al. | |

FOREIGN PATENT DOCUMENTS

| | | | |
|---|---|---|---|
| WO | 2005046802 A2 | 5/2005 | |
| WO | 2009/145463 A2 | 12/2009 | |
| WO | 2015069462 A1 | 5/2015 | |
| WO | 2015100403 A2 | 7/2015 | |

OTHER PUBLICATIONS

King, Kevin W., "The Design and Application of Wireless MEMS Inertial Measurement Units for the Measurement and Analysis of Golf Swings", 2008, University of Michigan. (Year: 2008).*

Huang, Peter Y et al., "Haptically Assisted Golf Putting through a Planar Four-Cable System", Jun. 21-24, 2011, IEEE World Haptics Conference, IEEE. (Year: 2011).*

Kelly, Philip et al, "A Virtual Coaching Environment for Improving Golf Swing Technique", Oct. 29, 2010, SMVC'10, ACM. (Year: 2010).*

International Search Report and Written Opinion dated May 22, 2018, in connection with International Patent Application No. PCT/US2018/018686, 17 pgs.

Penner, A.R., The Physics of Putting, Canadian Journal of Physica, 80:1-14, 2002.

International Search Report and Written Opinion dated Jun. 8, 2018, in connection with International Patent Application No. PCT/US2018/018686, 17 pgs.

Elevation and point data. gis.stackexchange.com. Online. Jan. 22, 2014. Acessed via the Internet. Accessed Nov. 8, 2018. < URL: https://gis.stackexchange.com/questions/83759/elevation-and-point-data>.

Rossman, Eileen et al., "Senior Project Spring 2016 Golf Putter Testing Mechanism", Dec. 12, 2016; California Polytechnic Status University, 96 pgs.

International Search Report and Written Opinion dated Jun. 22, 2018, in connection with International Patent Application No. PCT/US2018021924, 17 pgs.

International Preliminary Report on Patentability dated Oct. 10, 2019, in connection with International Patent Application No. PCT/US2018/018686, 11 pgs.

A. R. Penner, "The Physics of Putting," Can. J. Phys. 80 (2002), XP009061018, pp. 83-96.

* cited by examiner

METHOD AND APPARATUS FOR PERSONALIZED PUTTING OF A GOLF BALL

TECHNICAL FIELD

The present invention relates to the game of golf and, more particularly, to a method and apparatus for a highly personalized putting experience.

BACKGROUND

Golf is a very popular sport but demanding in terms of the various skills that need to be applied by the individual golfer to play the sport at even the most basic level. A golfer's basic swing technique is governed by many variables including his (or her) coordination and strength, golf club selection, golf ball selection, and golf course conditions, to name just a few.

In view of these many variables, the golfer is required to develop and maintain a certain skill set to improve their overall ability to play golf at some consistent level. For example, with respect to the putting element of the golf game, the player is faced with and required to determine and control variables such as stroke, speed, aim with respect to the golf ball, and aim (including putter angle) with respect to the face of the putter. Interestingly, it has been reported that putting comprises a large percentage (e.g., 25-30 percent) of the overall number of strokes made during a standard round of golf, and a putt, in both professional golf tournaments and recreational play, can create some of the greatest drama during a round as reflected in the well-known golf adage "drive for show, putt for dough" that is often repeated by golf professionals, amateurs, spectators and broadcasters.

As those who are well-acquainted with golf will attest, the ability to accurately and consistently putt a golf ball is a very difficult skill to develop and maintain, and many golfers are on a continual search to find their best and repeatable putting stroke. Seizing on an opportunity, the golf industry is replete with a variety of putting training devices to assist players with their putting prowess. Some of these devices are directed to improving aiming capability, others for improving alignment, and others for perfecting the stroke itself. Some devices attached to the putter itself or require the player to secure himself to the device or training apparatus.

The information directed to, and useful for, putting in these types of aides varies widely in terms of assisting a golfer in training for a particular putting stroke or executing a real-time putt during a round of golf. So, while some existing golf aides may be useful in providing general information related to putting, the golfer is still challenged with digesting the general information and effectively utilizing that information to determine how to strike a particular golf putt in a real-time fashion. Important to that real-time determination is the precise location of the golf ball on the green, the precise location of the golf cup (or hole), the overall surface characteristics of the green (including its topography and so-called green speed), and the ideal putt defined in terms of aiming direction and speed.

Therefore, a need exists for an improved putting stroke apparatus and methodology that determines and simulates the proper putting stroke in terms of aiming direction and speed for successfully making a putt based on particular putting green characteristics and the location of the golf hole on the putting green, and which is interactive with the user thereby providing an enhanced playing experience.

BRIEF SUMMARY OF THE EMBODIMENTS

In accordance with various embodiments, method and apparatus is provided that determines and simulates the proper putting stroke using at least aiming direction and speed for successfully making a particular putt based on particular putting green characteristics and the location of the golf hole on the putting green, and which is interactive with the user thereby providing an enhanced playing experience and improved putting results.

In accordance with an embodiment, a library of putting information is compiled using, illustratively, a pendulum putter apparatus and putting diagnostic tool wherein the putting information includes the approximate vertical angle necessary for a golf putter to be drawn back to exert the amount of force needed to roll the golf ball the required distance on the golf green using a pendulum motion. In turn, the compiled library of putting information can be used to customize a particular putting experience for a user (e.g., golfer). In accordance with an embodiment, the golfer will utilize a mobile device (e.g., smartphone) for initiating operations (e.g., through the execution of a mobile application) that will (i) initiate a calibration process involving the player attempting a set number of putts (e.g., 10 putts) at a specified distance and green speed, and for each putt, capture and calculate certain mobile device operational information (e.g., information from a micro electrical mechanical system (MEMS) integrated in the mobile device) at the time of each putt and the associated putting stroke applied by the player; (ii) calculate an average value, for the player, for a plurality of MEMS offset measurements; (iii) compare the calculated average player value with that of the compiled library of putting information for the same putt distance and same green speed to identify a set of precise distance guidance (e.g., a tempo and a vertical angle needed to make the putt at the specific distance); and (iv) using a feedback mechanism (e.g., haptic feedback resident on the mobile device) communicate the set of precise distance guidance to the player in order for the player to apply a putting stroke to make the putt successfully.

These and other advantages of the invention will be apparent to those of ordinary skill in the art by reference to the following detailed description and the accompanying drawings.

DETAILED DESCRIPTION

In accordance with various embodiments, method and apparatus is provided that determines and simulates the proper putting stroke using at least aiming direction and speed for successfully making a particular putt based on particular putting green characteristics and the location of the golf hole on the putting green, and which is interactive with the user thereby providing an enhanced playing experience and improved putting results.

In accordance with an embodiment, a pendulum putter apparatus is coupled with a putting diagnostic tool wherein the putting diagnostic tool determines at least an aiming direction and initial ball speed for a particular putt using at least four (4) inputs: (i) topographic information (e.g., contours) specific to the green; (ii) the green speed at a particular time; (iii) the golf hole location (i.e., the physical location of the golf hole); and (iv) the golf ball location on the green (i.e., the physical location of the golf ball). In this way, the pendulum putter apparatus is utilized with a calculated horizontal direction for aiming the putt at the golf hole and the initial ball speed needed to successfully make the putt by striking the golf ball in a pendulum motion. As will be appreciated the putting diagnostic tool may be configured in a variety of combinations of hardware and software executed thereon and the embodiments detailed herein below are illustrative but limiting in nature. Before describing an embodiment of the putting stroke apparatus, the method and operations of the putting diagnostic tool will be discussed in detail.

Figure 1A:
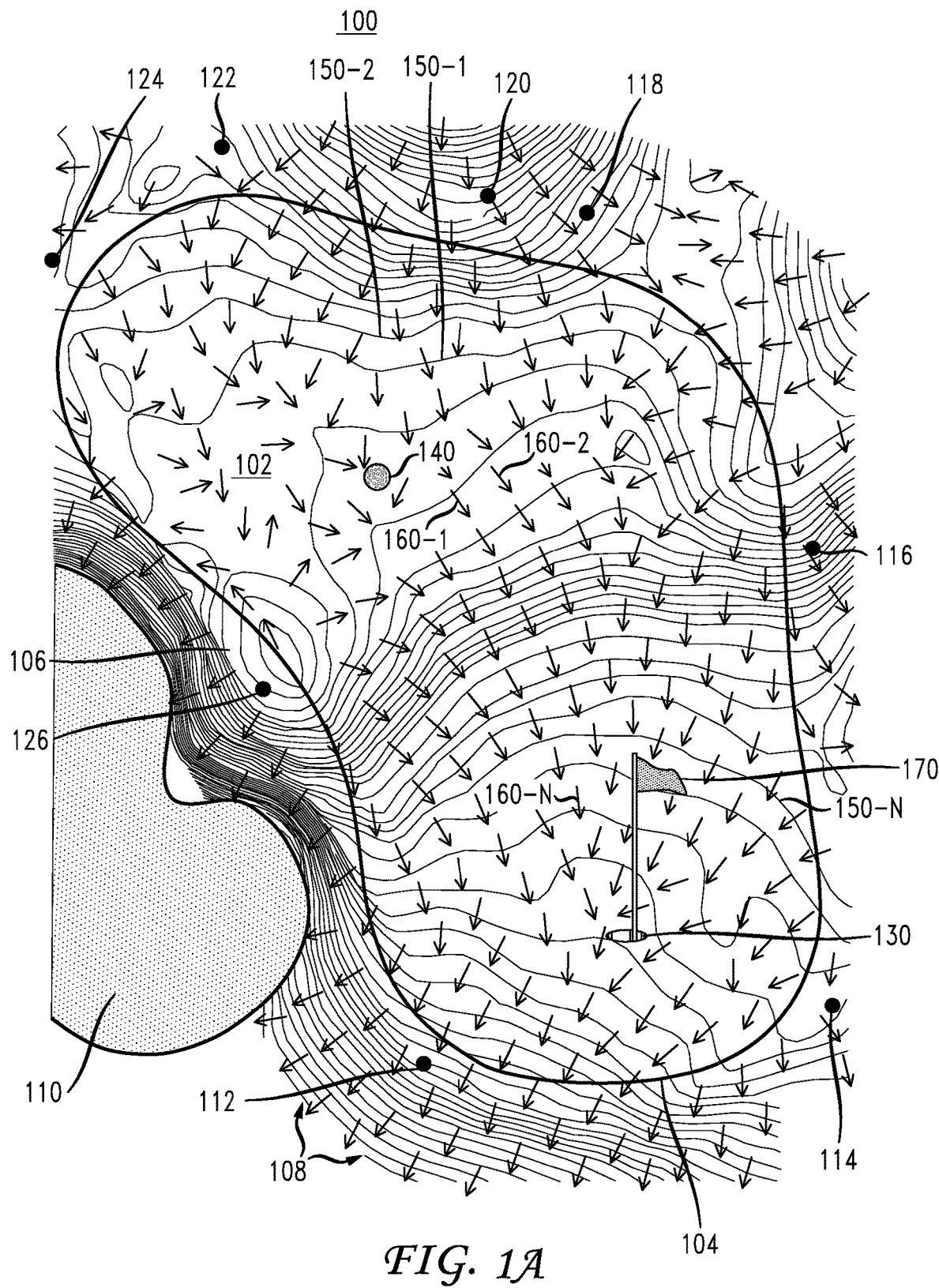
FIG. 1A shows an illustrative contour map generated and configured in accordance with an embodiment.

As noted above, in accordance with an embodiment, one input utilized by the putting diagnostic tool is topographic information (e.g., contours) specific to the green. Illustratively, this input comprises a plurality of three dimensional (3D) coordinate triples that facilitate the generation of a surface model of a golf green. FIG. 1A shows an illustrative contour map 100 generated and configured in accordance with an embodiment. Contour map 100 is one such exemplary input for the putting diagnostic tool in terms of identifying the requisite input of a plurality of 3D coordinate triples.

As shown, green 102 is an individual green, which in accordance with a typical golf course layout would be one of eighteen (18) greens located therein. Green 102 has a border 104 (or sometimes called a transition area) that transitions the green surface (typically the shortest cut of grass on a golf course and different type of grass) through a fringe 106 (typically an area having another cut of grass different from the green and immediately surrounding the green surface) and thereafter to a fairway 108 (typically a different cut of grass from the green and fringe area as well as a different type of grass). The surface contour of a green remains substantially unchanged after the original construction of the green (of course, nothing would preclude a contour change should a change in the surface topography be warranted or desired) such that so-called contour lines 150-1, 150-2 through 150-n and so-called "falls" indicated by directional lines or arrows 160-1, 160-2 through 160-n are established and can be recorded for reference. As will be appreciated, such contour lines and directional lines or arrows (the directional lines or arrows being a derivative of the contour lines) are important indicators with respect to the specific contour of a green in terms of characteristics such as shape, speed, slope and break. Green 102 is also shown having bunker 110 which is typically filled with sand and which captures golf shots that miss landing and/or staying on green 102.

In order to properly irrigate a golf course (e.g., areas such as green 102, fringe 106 and fairway 108), it is typical to use a network of sprinklers that periodically (e.g., on an automated schedule) water these various areas for a predetermined time period. Illustratively, this sprinkler network is defined, in part, by a plurality of sprinkler heads 112-126 that encircle and are located proximally to green 102, and are permanently embedded throughout fringe 106 and fairway 108 in some predetermined configuration to deliver the desired irrigation. The plurality of sprinkler heads 112-126 (and, as will be appreciated, the broader sprinkler network across a given golf course of which they form a part of) constitute a set of fixed reference points when their 3D coordinates have been determined in a suitable coordinate system (e.g., a localized 3D Cartesian coordinate system). In this way, the plurality of fixed reference points (e.g., the plurality of sprinkler heads 112-126) may be utilized to determine the location of a target (e.g., golf ball 140 or golf hole 130) on green 102. One technique using such fixed reference points is described in U.S. patent application Ser. No. 14/581,389, which is hereby incorporated by reference for all purposes. It will be understood that other fixed objects proximate to or near green 102 can also be used to determine the target location (provided that their 3D coordinates have been predetermined and that they are physically stable so that their coordinates remain substantially constant in time) including, but not limited to, drain covers, placards, signage, structures, grandstands, and equipment.

As shown, golf hole 130 is cut into green 102 with flagstick 170 (or sometimes also referred to as the "pin") set therein, and golf ball 140 is located on green 102. As will be appreciated, the location of golf cup 130 can change from day-to-day for any given golf course but typically not within the same day or golf round. As described above, the principles of the various embodiments are directed to determining and simulating the proper putting stroke in terms of aiming direction and initial ball speed for successfully making a particular putt (in this example, the putt of golf ball 140 to golf hole 130) based on the particular putting green characteristics of green 102 and the location of golf hole 130 thereon.

The generation of contour map 100 may be accomplished using a variety of well understood techniques. For example, a survey of green 102 may be undertaken using well-known surveying instruments such as a level and total station. The resulting surveying will enable the generation and output of a listing of 3D point records which can be utilized for the generation of a 3D surface model used by the putting diagnostic tool herein as input. As will be appreciated, other techniques that utilize non-traditional surveying instruments (e.g., cameras for close-range photogrammetry, Global Navigation Satellite System (GNSS) receivers in Real-Time Kinematic (RTK) mode, light detection and ranging (Lidar), and 3D laser scanners) may also be used to generate the aforementioned survey provide that the resulting 3D point records and other associated data is of sufficient accuracy.

As noted above, in accordance with an embodiment, a second input utilized by the putting diagnostic tool is the green speed at a particular time, for example, the speed of green 102. One well-known technique for measuring green speed is the use of a so-called "Stimpmeter" which is a tool utilized by the United States Golf Association (a well-known, established and recognized golf governing body in the United States). The tool is basically an inclined plane with a V-groove running down its center and a notch near the top that allows a golf ball to remain stationary until lifted to a certain height where the force of gravity causes the golf ball to roll out of the notch and down the plane. Such operation then assumes the golf ball reaches the surface of the golf green at a known speed; thus measuring the distance traveled in feet characterizes the speed of the golf green (e.g., slow, medium, fast). For example, some of the fastest greens in the world measure readings of 13-15 feet (4.0-4.6 m) on the Stimpmeter.

As noted above, in accordance with an embodiment, third and fourth inputs utilized by the putting diagnostic tool are related to the golf hole location (e.g., the physical location golf hole 130); and the golf ball location on the green (e.g., the physical location of golf ball 140). These respective locations (i.e., location coordinates of each) are determined in the same coordinate system as the survey for contour map generation as described above, and may be located, illustratively, using a GNSS receiver in RTK mode. As will be understood, GNSS receivers provide locations (e.g., 3D coordinates) in a global geodetic coordinate system. In the embodiments herein, the putting diagnostic tool requires 2D coordinates in a local coordinate system. As such, the 3D geodetic coordinates must be transformed to 2D coordinates in the local system. This transformation will be readily understood by those skilled in the art and may take various forms.

For example, the coordinates provided by the GNSS receiver can be expressed in both an Earth-Centered Earth-Fixed (ECEF) Cartesian system (i.e., X, Y, Z coordinates) or, given by an associated reference ellipsoid in a geodetic coordinate system using latitude, longitude, and height (i.e., $\varphi$, $\lambda$, h). In either case, the 3D coordinates from the GNSS receiver must be mathematically transformed to the coordinate system of the golf green (e.g., green 102), which can be separated into planar components (x, y) and a height component H. Such a transformation can be made by determining certain parameters which will now be discussed.

To determine the transformation parameters, coordinates of a set of physically accessible points on the ground must be "known" at a sufficient accuracy level in both the geodetic and local coordinate systems, which are based on a triad of orthogonal axes. To transform between two 3D coordinate systems, estimated parameters such as three translation, three orientation, and one scale parameter are typically used. In accordance with the embodiments herein, the 2D planar coordinates (x, y) in the local coordinate system are necessary in order to accurately determine the location of the golf hole and golf ball.

As will be appreciated, over a small or local neighborhood/area (e.g., golf green 102) the global geodetic coordinates (i.e., $\varphi$, $\lambda$, h) from the GNSS receiver can be rotated into a local geodetic (Cartesian) coordinate system (N, E, U) with a specified origin point in the vicinity of the rotated points. In this way, the local geodetic and local coordinate system (i.e., the local coordinate system for golf green 102) may be assumed to have a common scale. As such, the transformation between their respective horizontal coordinates (N, E) and (x, y) can be represented by three parameters: two translation and one orientation. In this case, only two control points with known coordinates in both coordinate systems are needed which leads to a unique determination of these three transformation parameters. Of course, having a redundant number of control points (i.e., more than two) will increase error detection abilities and potentially improve the overall accuracy of the transformation parameter estimation.

As noted above, the coordinates provided by the GNSS receiver can be expressed in both an ECEF coordinate system (with axes labeled X, Y, 4, or given an associated reference ellipsoid, in a geodetic coordinate system expressed as latitude, longitude, and height above the ellipsoid (i.e., $\varphi$, $\lambda$, h). The meaning of ECEF is that the origin O is at the center of mass of the Earth. The X and Y axes lie in the equatorial plane. The X-axis points to the prime meridian; the Z-axis coincides with the Earth's spin axis, and the Y-axis completes a right-handed orthogonal coordinate system.

Figure 1B:
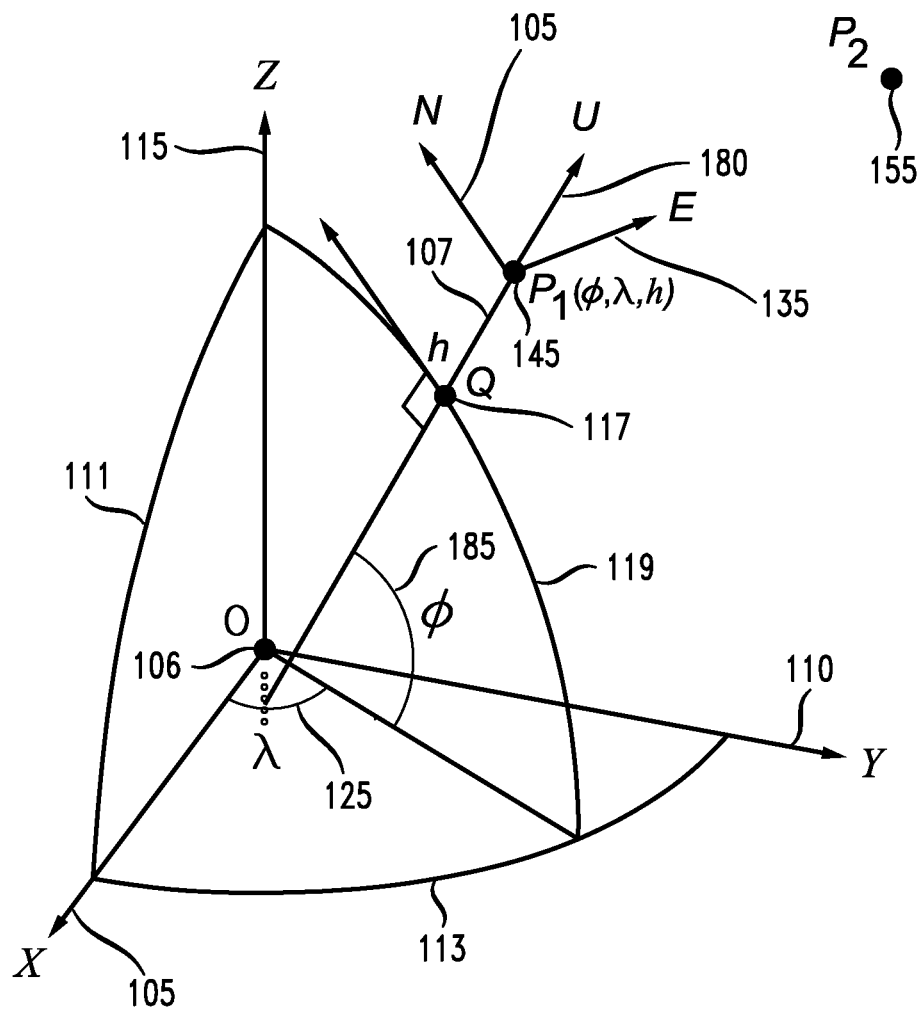
FIG. 1B shows a global geodetic system in an Earth-Centered Earth-Fixed reference frame and a local geodetic coordinate system in accordance with an embodiment.

FIG. 1B shows a global geodetic system in an ECEF reference frame, and a local geodetic (LG) coordinate system (as further described below) in accordance with an embodiment. In addition, portions of two median lines and the equatorial plane of a reference ellipsoid (e.g., WGS 84) are shown. As will be appreciated, FIG. 1B is not shown to scale, as the equatorial radius of the WGS 84 ellipsoid is 6,378,137 meters, and the distance between two points, for example, point $P_1$ 145 and point $P_2$ 155 (which are assumed to lie on or near the same golf green, e.g., green 102) may only be a few to several tens of meters. As shown, FIG. 1B depicts the ECEF origin (O) point 109 together with X-axis 105, Y-axis 110, and Z-axis 115, and the LG coordinate system with axes north axis N 105, east axis E 135, and up axis U 180, and point $P_1$ (e.g., the point associated with sprinkler head 116 on green 102) latitude 185, longitude 125, and height above ellipsoid 107 (i.e., $\varphi$, $\lambda$, h). A reference ellipsoid is depicted by showing a portion of the prime meridian 111, a meridian 119 containing an ellipsoid normal passing through point $P_1$ 145, and a portion of the equatorial plane 113. Point Q 117 lies on the reference ellipsoid and on the normal line through $P_1$ 145; thus, the height above the ellipsoid h at point $P_1$ 145 is the distance between points Q 117 and $P_1$ 145 along the normal line.

Given values of certain parameters of the reference ellipsoid (e.g., its equatorial radius and flattening values), there is a one-to-one mapping between the Cartesian coordinates (i.e., X, Y, Z) and the geodetic coordinates (i.e., $\varphi$, $\lambda$, h), the mathematical relationships and formulas for which are well-known by those skilled in the art. Further, over a small or local neighborhood (e.g., green 102), it is also well-known that ECEF coordinate differences (e.g., as derived from a GNSS receiver) can be rotated into a LG coordinate system. The coordinate differences are computed between a point designated as the origin of the LG system and other points that must be located with respect to that origin point. For example, up axis U 180 in an LG coordinate system coincides with the normal to the ellipsoid at the origin of the LG system, and north axis N 105 is parallel to the direction from point Q 117 to geodetic north, and east axis E 135 completes an orthogonal left-handed coordinate system.

By way of illustration, given $P_1$ 145 with coordinates $(X_1, Y_1, Z_1)$ which may be, for example, associated with a sprinkler head (e.g., sprinkler head 116) near green 102 is located with a GNSS receiver (not shown) and is designated as the origin an LG coordinate system. Given a second point $P_2$ 155 with coordinates $(X_2, Y_2, Z_2)$ in the vicinity of $P_1$, which is also located with the GNSS receiver to thereby locate points $P_1$ 145 and $P_2$ 155, respectively, in the ECEF coordinate system. As noted above, $P_1$ 145 with coordinates $(X_1, Y_1, Z_1)$ can readily be converted to $P_1$ 145 $(\varphi_1, \lambda_1, h_1)$, where $(\varphi_1, \lambda_1, h_1)$ are geodetic coordinates. Next, let the difference in coordinates between points $P_1$ 145 and $P_2$ 155 (i.e., a 3D vector from $P_1$ 145 to $P_2$ 155) in the ECEF coordinate system be defined as follows:

$$[\Delta X, \Delta Y, \Delta Z]^T = [X_2 - X_1, Y_2 - Y_1, Z_2 - Z_1]^T$$

In this way, the LG coordinates $(N_2, E_2, U_2)$ of $P_2$ 155 are given by the matrix equation:

$$\begin{bmatrix} N_2 \\ E_2 \\ U_2 \end{bmatrix} = R(\emptyset, \lambda) \begin{bmatrix} \Delta X \\ \Delta Y \\ \Delta Z \end{bmatrix}, \quad (1)$$

$$\text{with } R = \begin{bmatrix} -\sin\emptyset\cos\lambda & -\sin\emptyset\sin\lambda & \cos\emptyset \\ -\sin\lambda & \cos\lambda & 0 \\ \cos\emptyset\cos\lambda & \cos\emptyset\sin\lambda & \sin\emptyset \end{bmatrix}.$$

Equation (1) can be applied to any number of points to compute their LG coordinates in a system having point $P_1$ 145 as its origin, as detailed above.

Ultimately, points located in the LG coordinate system must be transformed into the coordinate system of the golf green (e.g., green 102), which can be separated into planar components (x, y) and height component H. Such a transformation can be made if certain parameters of the transformation can be determined (i.e., estimated). To estimate the transformation parameters, coordinates of a set of physically accessible points on the ground must be "known" to an acceptable level of accuracy in both of the coordinate systems (one being the LG coordinate system provided by the GNSS receiver via the transformation in equation (1), and the other being the coordinate system associated with the golf green), which may have been established previously using conventional, well-known surveying methods. Herein, such points are deemed "control points", and assuming that coordinates in both systems refer to a triad of orthogonal axes, seven transformation parameters could be estimated (namely, three translation, three orientation, and one scale factor).

However, in accordance with the various embodiments herein, only the 2D planar coordinates (x, y) in the coordinate system associated with the golf green (e.g., green 102) are needed for the location of the cup (e.g., golf cup 130) and golf ball (e.g., golf ball 140) in a horizontal plane. As such, assuming that the horizontal axes of the LG system (i.e., north axis 105 and east axis 135) lie in a plane common to the golf green's coordinate system, then the 2D transformation between their respective coordinates (N, E) and (x, y) can be represented by the following four parameters: two translation, one rotation, and one scale factor. In such a case, only two control points with known coordinates in both coordinate systems are needed, which would permit a unique determination of the four transformation parameters. However, having a redundant number of control points (i.e., more than two) would allow for a better chance to detect potential errors in the given coordinates and could also result in a more precise estimation of the four transformation parameters. Note that the assumption of a common plane is not necessarily strictly satisfied, as the NE-plane is orthogonal to an ellipsoidal normal passing through the points of origin $P_1$ 145, whereas the xy-plane might be assumed to be normal to the tangent to a plumb line at the same point. The difference between the ellipsoid normal and the tangent to the plumb line is called the "deflection of the vertical", and for purposes of the various embodiments herein is considered to be sufficiently small so as to be ignored.

Given a set of n physical control points $(P_1, P_2 \text{ through } P_n)$ having known 2D coordinates in both an LG coordinate system and a golf-green coordinate system, an estimation may be made with respect to so-called unknown transformation parameters $\xi = [\xi_0, \xi_1, \xi_2, \xi_3]^T$ necessary to transform from the LG coordinate system to the golf green's coordinate system using the following mathematical model:

$$\begin{bmatrix} x_1 \\ y_1 \\ x_2 \\ y_2 \\ \vdots \\ x_n \\ y_n \end{bmatrix} \approx \begin{bmatrix} 1 & 0 & E_1 & -N_1 \\ 0 & 1 & N_1 & E_1 \\ \vdots & \vdots & \vdots & \vdots \\ 1 & 0 & E_n & -N_n \\ 0 & 1 & N_n & E_n \end{bmatrix} \begin{bmatrix} \xi_1 \\ \xi_2 \\ \xi_3 \\ \xi_4 \end{bmatrix}. \quad (2)$$

The variables in equation (2) are defined as follows:

$(x_i, y_i)$—Coordinates of point $P_i$ in the target system (i.e., golf green).

$(N_i, E_i)$—Coordinates of point $P_i$ in the source system (i.e., LG).

$\xi_0$—Translation parameter along the x-axis in the target system.

$\xi_1$—Translation parameter along the y-axis in the target system.

$\xi_3$—Auxiliary parameter $\omega \cdot \cos \alpha$.

$\xi_4$—Auxiliary parameter $\omega \cdot \sin \alpha$.

$\omega$—Scale parameter between the two coordinate systems.

$\alpha$—Rotation angle parameter between the two coordinate systems.

The approximately equal sign in equation (2) above is used to denote that the coordinates in both systems contain random measurement errors, which can be accounted for by well-known least-squares estimation techniques, thereby requiring that the number of points n be greater than two (n>2). After estimation of the parameter vector $\xi$, the estimated rotation angle $\hat{\alpha}$ can be computed by $\hat{\alpha} = \arctan(\hat{\xi}_4 / \hat{\xi}_3)$, while $\hat{\omega} = \sqrt{\hat{\xi}_2^2 + \hat{\xi}_3^2}$ yields the estimated scale factor. Note that estimated variables are shown with hats. Optionally, the scale factor w can be constrained to one by adding $\xi_2^2 + \xi_3^2 = 1$ as a constraint to the model in equation (2).

Figure 1C:
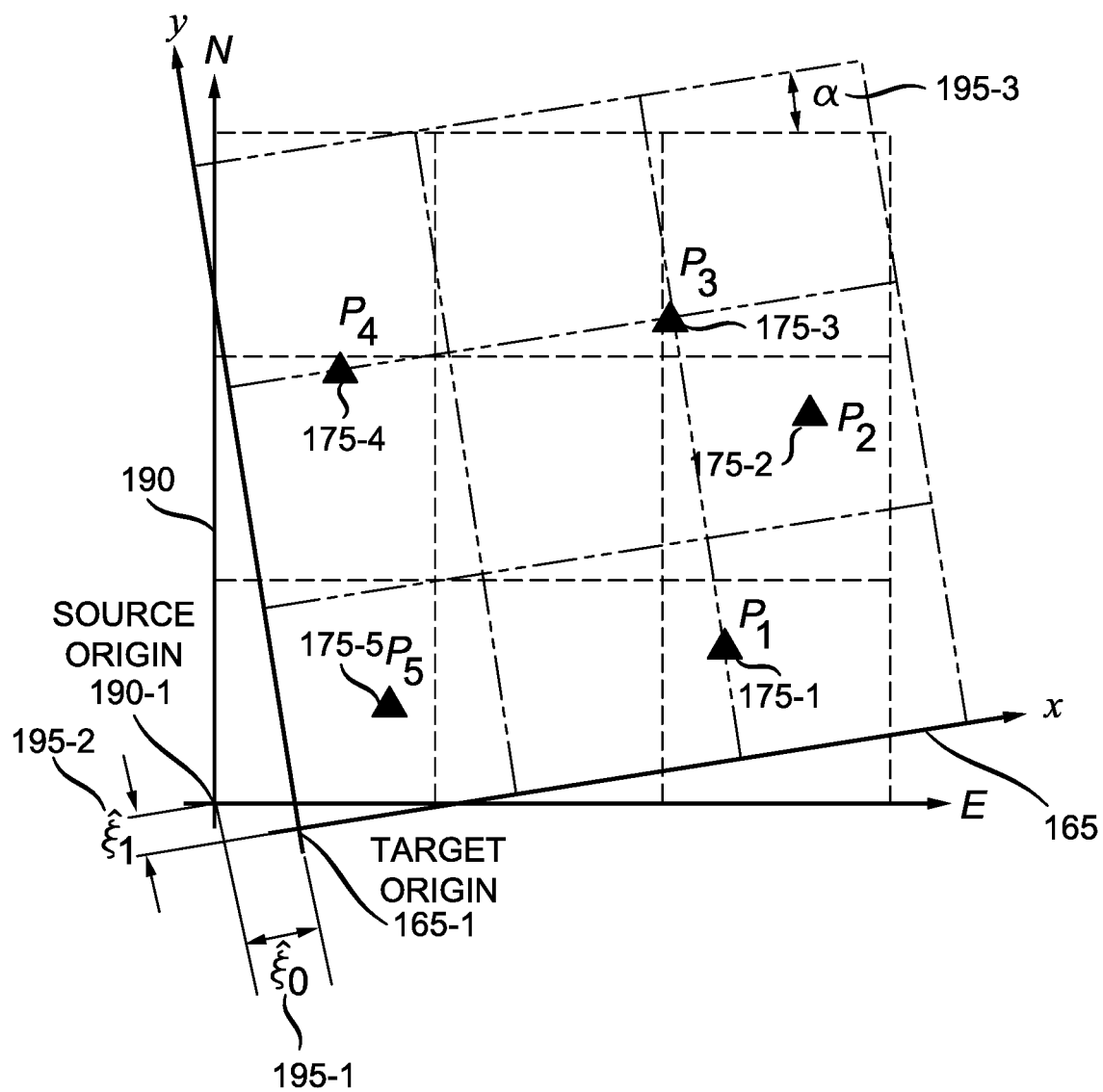
FIG. 1C shows a local geodetic coordinate system with a source origin, and a golf-green coordinate system with a target origin in accordance with an embodiment.

For example, in terms of the illustrative computations described herein above, FIG. 1C shows LG coordinate system 190 with source origin 190-1, and golf-green coordinate system 165 with target origin 165-1. Also shown in FIG. 1C are estimated transformation parameters 195-1, 195-2, and 195-3 together with five exemplary control points, 175-1, 175-2, 175-3, 175-4, and 175-5.

Figure 2:
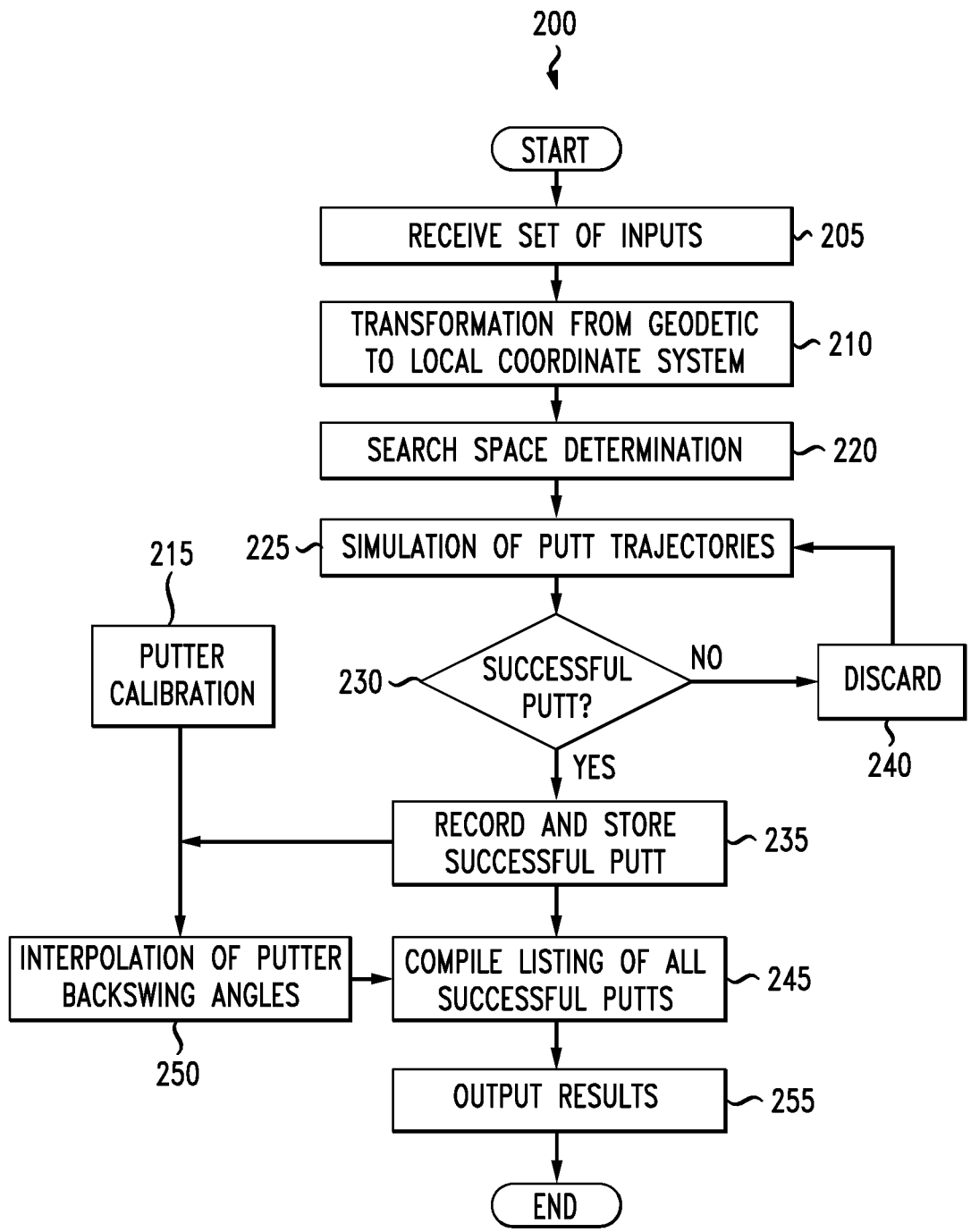
FIG. 2 shows a flowchart of illustrative operations for determining and simulating a precise putting stroke in accordance with an embodiment.

FIG. 2 shows a flowchart of illustrative operations 200 for determining and simulating a precise putting stroke in accordance with an embodiment. As detailed above, at step 205, the required set of inputs (i.e., contour map/3D surface model, golf hole location, golf ball location, and green speed) are received. At step 210, based on the received inputs, the geodetic to local coordinate system transformation is undertaken as described above. At step 215, a putter calibration is performed and such calibration is specific to the particular type of putter unit being used to strike the putt. In accordance with an embodiment, the calibration is undertaken using specific starting and stopping positions of the golf ball travelling across the golf green surface as captured by, illustratively, a conventional total station survey instrument in any number of well-known manners. The calibration of step 215 is illustratively a one-time operation (or an infrequent operation) that may be performed independent of any real-time use of putter unit. For example, the calibration may be performed in a factory setting or other facility thereby providing for calibration of a variety of putter units including but not limited to configuration of pendulum putter apparatus 400. The measurements are taken at various putter backswing angles which are deemed so-called "measured values". Multiple measurements are made for a given backswing angle and the measured final stopping positions are averaged using a well-known distance-weighted mean formula. Using the position given by the distance-weighted mean, well-known principles of physics (see, e.g., Penner, A. R., The Physics of Putting, Can. J. Phys. 80:1-14, 2002; hereinafter "Penner") are used to identify a putt with an initial ball speed and aiming angle which match the starting and stopping positions of the golf ball. The derived initial ball speed and given backswing angle are then used to estimate the parameters of a fitted nonlinear function (as further detailed herein below), and the fitted function can be interpolated to compute the backswing angle associated with any initial ball speed thereby completing the calibration and outputting a set of putter calibration parameters (e.g., a record describing the type of fitted function and the numerical values of the estimated parameters associated with the fitted function).

In a further embodiment, the calibration at step 215 is alternatively performed by measuring the average ball speed between two closely spaced light gates on a low-friction surface which is considered to be approximate to a measurement of initial ball speed (i.e., upon contact). These measurements are taken at various putt backswing angles and deemed "measured values" and used to estimate the parameters of a fitted nonlinear function (as further detailed herein below), and the fitted function can be interpolated to compute the backswing angle associated with any initial ball speed thereby completing the calibration and outputting a set of putter calibration parameters. In an exemplary configuration, the two light gates are configured at a fixed distance, and without any horizontal coupling such that a first light gate is situated at a position which is a few millimeters from the initial launch point of the golf ball (i.e., stationary position before being struck) and the second light gate is situated approximately 50 centimeters from the first light gate's position. In this way, once the golf ball (e.g., golf ball 455) is struck using pendulum putter apparatus 400, the golf ball will travel (and deaccelerates through) a total distance of approximately 50 centimeters as the golf ball passes by the respective light gates. In a further calibration embodiment, the above-described light gates are replaced with a conventional camera.

As noted above, the data collected in the calibration at step 215 is fitted to a nonlinear function, for example, a polynomial of second degree or higher. If the initial ball speed or distance and backswing data are considered as measurements containing random errors, in accordance with an embodiment, a well-known total least-squares (TLS) data adjustment can be used to estimate the unknown parameters of the function. In accordance with a further embodiment, where the swing back angles are treated as errorless data, the well-known ordinary least-squares (OLS) method can be used to estimate the unknown parameters. In either case, the estimated parameters will be utilized for the interpolation of backswing angles at step 250 where using the aforementioned putter calibration parameters and an initial ball speed (e.g., as output by step 235 as detailed below), the backswing angle for a particular putt is computed by interpolation of the fitted function/polynomial set forth in step 215.

In accordance with the embodiment, at steps 220 through 240, a simulation is undertaken that determines the precise trajectory of a golf putt on a particular golf green (i.e., the modeled surface) given the initial speed, and direction (i.e., the initial velocity) of the golf ball. Trajectories are determined by numerical integration of the location and velocity of the golf ball struck with a specified initial velocity. At each integration step, the location and velocity are updated, and the integration continues until the golf ball comes to rest (i.e., zero velocity). The simulation accounts for primary forces (and discounts certain secondary forces) acting on the golf ball along its path, in particular, surface friction and gravity due to sloping terrain. In the course of the integration, a determination is made as to whether the golf ball intersects the so-called "capture region" of the golf cup (i.e., where the golf ball is expected to drop into the golf hole), and if so, that putt is deemed as "successful", otherwise the putt is deemed "unsuccessful". In accordance with the embodiments, the integration is repeated for a range of initial directions and speeds, and for suitable interval (e.g., left 30° to right 30° and 2.3 to 2.9 m/s to ensure that a plurality of successful putts are determined.

At step 220, a search space determination is made. In particular, in accordance with the embodiment, the simulation performed will search over a 2D space comprised of speed and direction for putt trajectories that will theoretically result in a successfully made putt. This search space must be sufficiently large to find one or more theoretically successful putts in order to identify the "best" putt(s) but must not be so large to as to adversely impact computational performance. In accordance with the embodiment, at step 220, this 2D search space is determined by establishing a range of initial ball velocities and determining the final velocity ($v_f$) at which the golf ball will drop into the golf cup (i.e., a successfully "made" putt) and remain therein (i.e., not bounce out of the cup). In terms of the well-known physics principles as previously discussed, for example, such final velocities, on a level surface, are known to be in the range of 0 to 1.63 m/s. Also, in accordance with the embodiment, the net slope of the golf green from the golf ball to the golf cup can be used to establish a maximum value of $v_f$, given that the intermediary sloping of the golf green is assumed to have consistent deceleration characteristics in Penner. More particularly, the minimum and maximum velocities are defined as follows:

$$0 < v_f < \frac{1.63}{\sqrt{1-\sin\theta}} \quad (3)$$

$$v_{min} = \frac{10}{7}gd(\rho_g\cos\theta + \sin\theta) \quad (4)$$

$$v_{max} = \sqrt{v_f^2 + v_{min}^2} \quad (5)$$

Here, d is the initial distance between the cup and ball, g is the magnitude of acceleration due to gravity, and θ is the net slope between them. The other terms in equations (1)-(3) are defined below.

At step 225, the simulation of putt trajectories is performed to determine potentially successful putts from unsuccessful ones based on the direction and speed characteristics as detailed above. In particular, the tangential force acting on the golf ball has a magnitude f and makes an angle φ with the y-axis, such forces and angle are given by:

$$\tan\varphi = \frac{\rho_g\cos\theta\cos\varphi\sin\beta - I_b\sin\theta}{\rho_g\cos\theta\cos\varphi\cos\beta - I_b\cos\theta\sin\varphi} \quad (6)$$

$$f = \frac{\rho_g\cos\theta\cos\varphi\cos\beta - I_b\cos\theta\sin\varphi}{(1+I_b)\cos\varphi}mg \quad (7)$$

where:
$\rho_g$ is an indicator of the rolling resistance of the green surface;
β is the direction of the ball travel;
θ is the slope of a plane along the y-axis;
φ is the slope of a plane along the x-axis;
$I_b$ is a component of the moment of inertia I, such that $I_b = m/R_2$, where R is the radius of the golf ball; and
g is the magnitude of the acceleration due to gravity g.
As will be appreciated, a certain number of simplifications (having only a secondary effect on golf ball trajectory) are reflected in the application of the above equations as noted in Penner: (i) the golf ball is taken to be in a state of pure rolling throughout its entire path and not accounting for any initial state of bounce in the golf ball, sliding, or a combination of sliding and rolling over a certain portion of its path to the golf hole; (ii) the surface of the golf ball is deemed smooth rather than dimpled; and (iii) the deceleration of the golf ball is taken as a constant thereby not accounting for any variable speeds.

Using the trajectory simulations, a determination is made at step 230 as to the success of a particular putt. Specifically, if it determined that the golf ball will fall within the capture region of the golf cup (alternatively referred to herein as golf hole) in the course of the specific trajectory, that putt is deemed "successful", at step 235, and recorded and stored for later use. If not, the putt is discarded at step 240 as "unsuccessful" and the simulations proceed as necessary. In this way, a listing of "successful" putts is compiled, at step 245, that contains the initial speed and aiming direction of all successful putts as determined by the executed simulations (at step 225) and used in the interpolations at step 250 as discussed above, and at step 255 the results are provided as output. The output, includes, illustratively, the putts ranked in ascending order of the distance of the resting point of the golf ball (i.e., as if there was no golf hole to interfere with the course of the golf ball), and the center of the golf cup. The ranking is established, illustratively, by at least two criteria. The first criterion is how close a particular putt approaches the "center" of the golf cup along its trajectory. The second criterion is how close the resting point of the golf ball is to a nearby point projected through the center of the cup and lying "X" feet beyond the cup, where X may be two (2) feet, for example. The putts that pass closer to the cup's center are considered to be more likely to succeed, than those further away from the center. Further, those putts that would come to rest nearer to the designated point beyond the cup may be considered more preferable than others.

Figure 3:
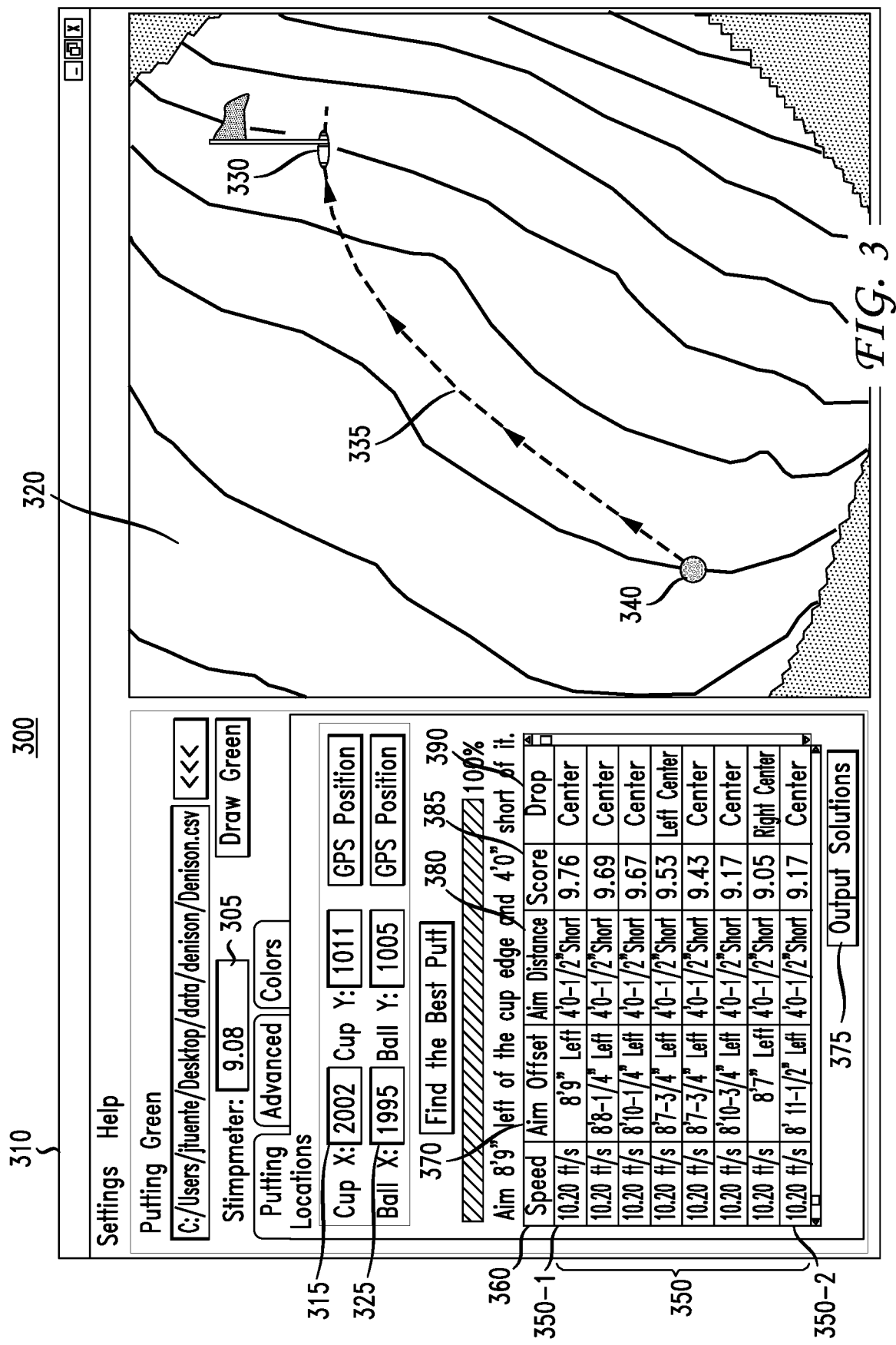
FIG. 3 shows exemplary results for determining and simulating a precise putting stroke in accordance with the operations of FIG. 2.

FIG. 3 shows exemplary results 300 for determining and simulating a precise putting stroke in accordance with the operations of FIG. 2 and using the illustrative pendulum putter apparatus of FIG. 4, as further discussed below. Illustratively, exemplary results 300 are outputted and displayed on display 310. Exemplary results 300 include contour map 320 showing golf hole 330 and golf ball 340, golf green speed (i.e., Stimpmeter value) 305, golf cup coordinates 315, golf ball coordinates 325, and the listing of putts 350 as generated and ranked, as detailed above. That is, putt listing 350-1 is ranked highest in the listing thereby designating that this putt (see, trajectory 335) is the one that is closest to the center and considered to be more likely to succeed than those further away from the center (e.g., the lowest ranked putt listing 350-2). Further details regarding the listing of putts 350 includes the speed 360, aim offset 370, aim distance 380, score 385 (used for designating a final rank), and drop 390 (designating position from center), and all the results may be outputted by the user, for example, by selecting "output solutions" 375 (e.g., a touchscreen radio button). In this way, these solutions can be utilized to demonstrate and execute actual putts with higher likelihoods of success.

More particularly, as noted above, a putting stroke apparatus and method is provided that determines and simulates the proper putting stroke in terms of aiming direction and initial ball speed for successfully making a particular putt based on particular putting green characteristics and the location of the golf hole on the putting green. Illustratively, a pendulum putter apparatus is coupled with a putting diagnostic tool, performing the operations detailed herein above, to determine an aiming direction and an initial ball speed for a particular putt.

Figure 4A:
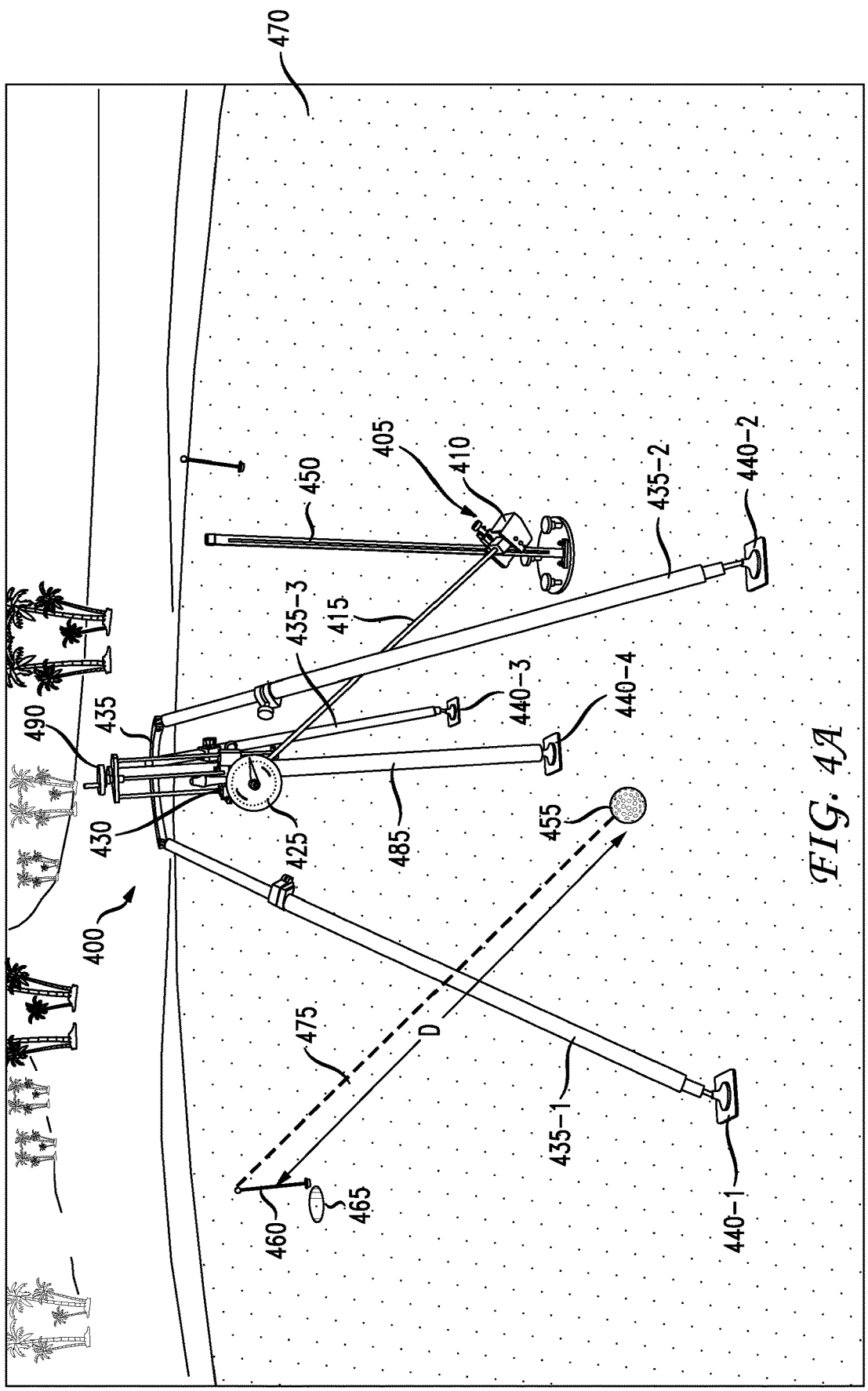
FIG. 4A shows a pendulum putter apparatus in accordance with an embodiment.
Figure 4B:
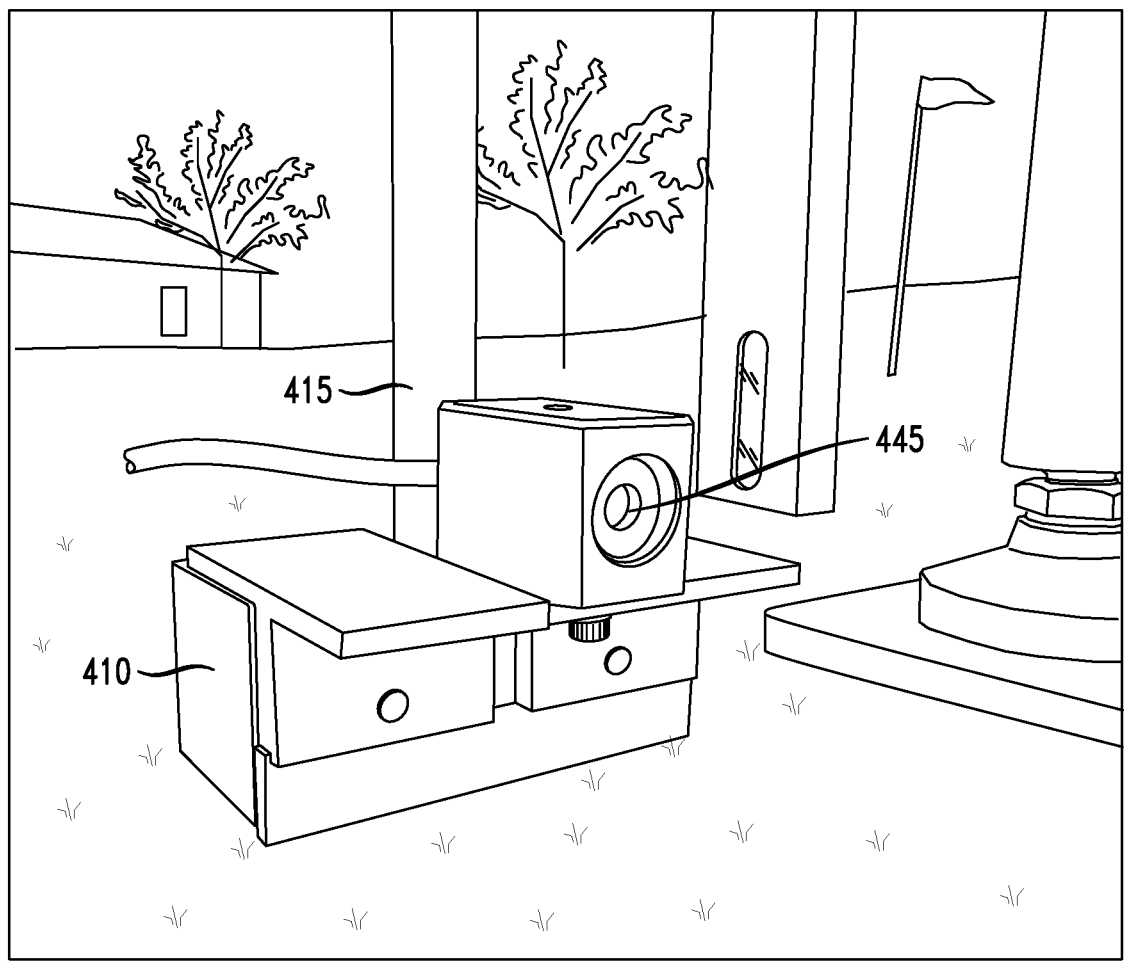
FIG. 4B shows a close-up view of the adjustable putter head and aiming mechanism of the pendulum putter apparatus shown in FIG. 4A.
Figure 4C:
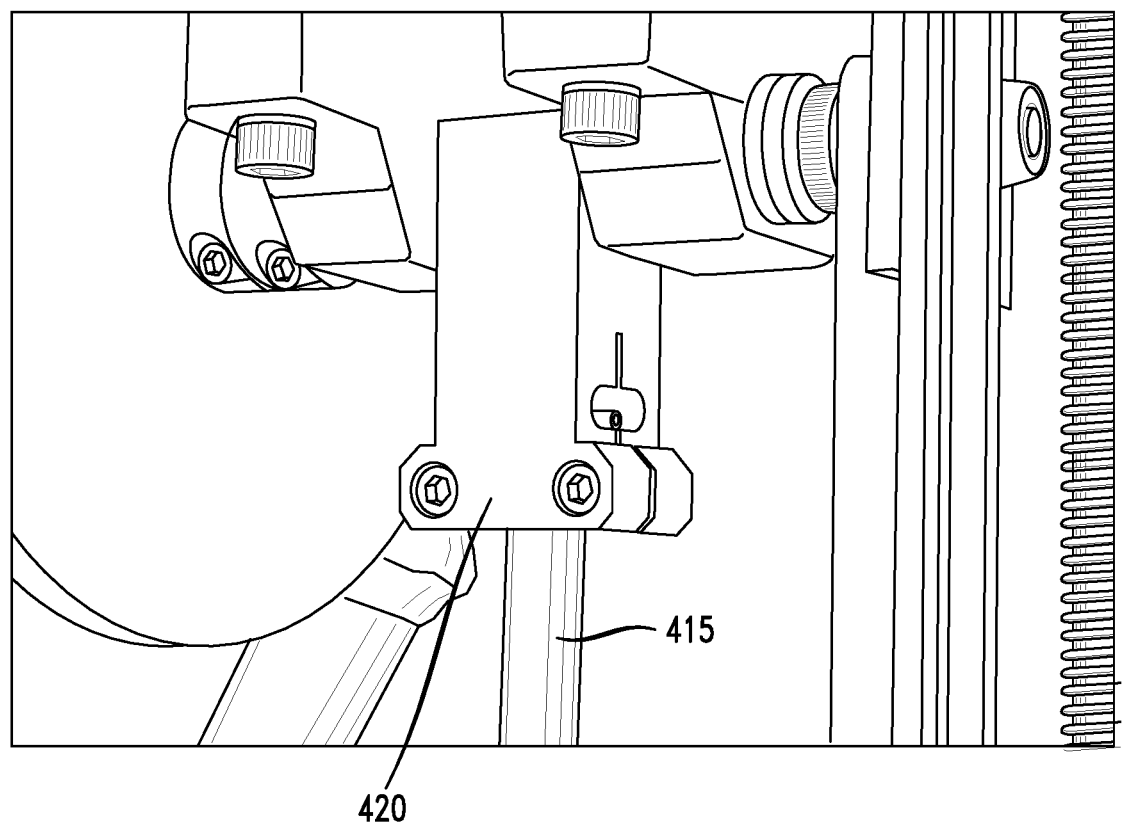
FIG. 4C shows a close-up view of the axle, trunnion, mounting bracket, and the adjustable putter shaft of pendulum putter apparatus shown in FIG. 4A.
Figure 4D:
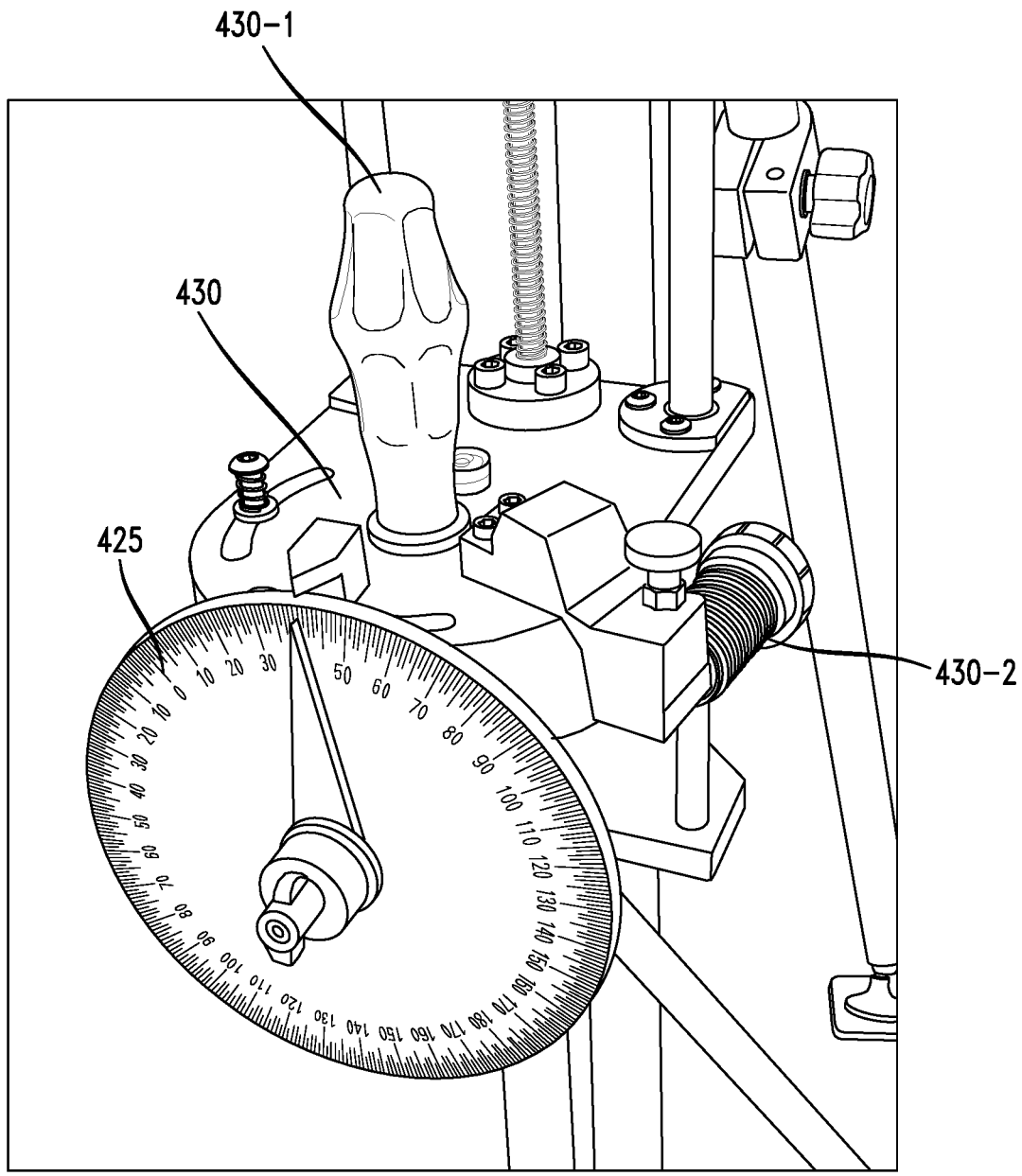
FIG. 4D shows a close-up view of the vertical angular scale and fine trigger adjustment assembly of pendulum putter apparatus shown in FIG. 4A.

To that end, FIG. 4A shows an illustrative pendulum putter apparatus 400 situated on golf green 470, the putter apparatus 400 comprising at least: (i) putter assembly 405 comprising adjustable putter head 410, adjustable putter shaft 415, and mounting bracket 420, with FIG. 4B showing a close up view of adjustable putter head 410 and FIG. 4C showing a close up view of mounting bracket 420; (ii) vertical angular scale 425 and fine trigger adjustment assembly 430-1 and 430-2, with a close up view shown in FIG. 4D; (iii) aiming mechanism 430 as shown in FIG. 4D; and (iv) stationary support assembly 435. In an embodiment, laser 445 is an optional feature which can be placed upon adjustable putter head 410 on putter shaft 415 to aid in aiming, as shown in the close up view of FIG. 4B and adjustable support arm 440 connected to vertical angular scale and fine trigger adjustment assembly 425 and extending to ground surface of green 470, with stationary support assembly 435 including three (3) supporting legs 435-1, 435-2, and 435-3 having individual feet 440-1, 440-2, and 440-3 configured, for example, in a tripod fashion, along with a supporting center post 485 and foot 440-4. As shown in FIG. 4D, aiming mechanism 430 includes knob 430-1 and tangent screw 430-2 to facilitate a coarse aiming by the user loosening knob 430-1 and rotating the assembly there below about the vertical axis. Using aiming mechanism 430, a finer adjustment is made possible by the user tightening knob 430-1 and engaging tangent screw 430-2. In addition, adjustable putter head 410 can be made to strike the ball at a particular point above the ground by turning handle 490 at the top of the apparatus 400, which allows putter assembly 405 to translate vertically. As such, pendulum putter apparatus 400 is a mechanical apparatus that is representative of any number of well-known commercially standard putters used by professional and/or amateur golfers.

In this way, pendulum putter apparatus 400 is configured for mimicking a human putter's putting stroke at some specified initial ball velocity and direction, as determined in accordance with the illustrative operations set forth in FIG. 2 and described above. Thus, upon being released from trigger stand 450, putter assembly 405 swings under the well-known force of gravity and under resistance primarily applied by friction between the axle upon which adjustable support arm swings about and the ball bearings that hold the axle in place. Illustratively, the ball bearings are set in two (2) opposing trunnions that are rigidly attached to the lower plate of a pair of plates that can be translated vertically along a pair of steel rods attached to supporting legs 435-1, 435-2, and 435-3.

Thus, the aiming direction of pendulum putter apparatus 400 (by and through putter assembly 415) is defined by the projection of the vertical plane that the putter apparatus swings into the horizontal plane tangent to the associated plumb line, as putter head 410 travels from a release point towards golf ball 455 in order to make contact therewith. Illustratively, the direction can be set by rotating a lower plate with respect to an upper plate of the pair of plates, as described above. If so configured, laser 445 is set square to putter head 410 using, for example, a mechanical bracket with magnets, and laser 445 illuminates target 460 which has been placed at some specified distance (D) 475 from golf cup 465 to indicate when the aiming direction of pendulum putter apparatus 400 is correct. In accordance with the embodiment, laser 445 is removed after the targeting is completed (i.e., establishing an initial orientation of putter head 410 in the horizontal plane) and before putter head 410 is drawn back to strike golf ball 455. Also, in various embodiments, a mirror (not shown) may be mounted on adjustable putter shaft 415 to facilitate the observation of the reflected laser beam (originating from laser 445) off target 460, and the mirror is also removed after targeting is completed. In accordance with a further embodiment, an initial aiming direction may be established using a set of conventional mechanical clamps and gears using coarse rotation of the lower plate followed by a more precise turning of the lower plate with respect to the upper plate of the pair of plates.

Figure 5:
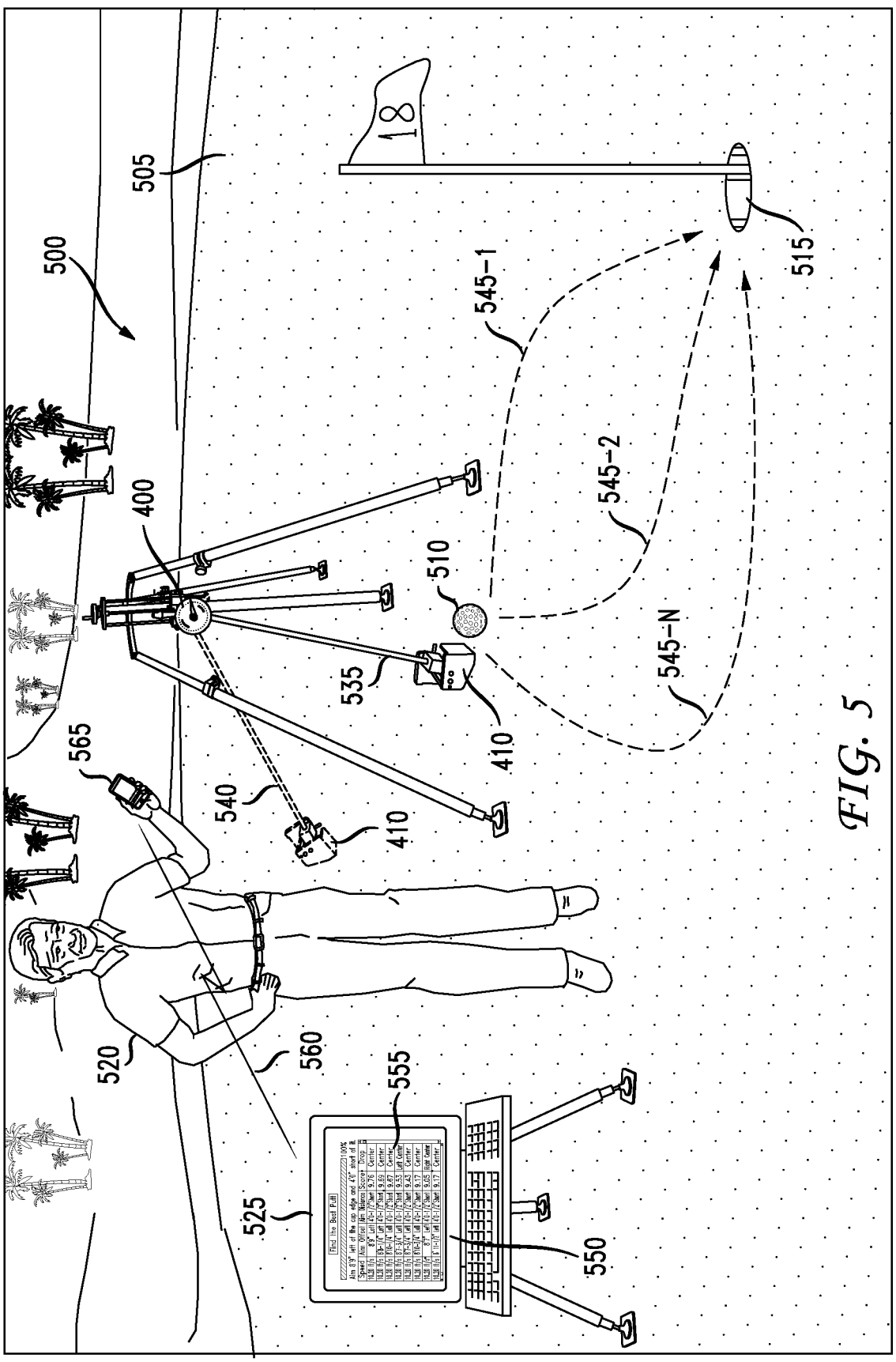
FIG. 5 shows an illustrative golf putting system in accordance with an embodiment.

FIG. 5 shows an illustrative golf putting system 500 in accordance with an embodiment that employs pendulum putter apparatus 400 (as detailed above) together with putting diagnostic tool 525. Putting diagnostic tool 525 can be any type of computing device (e.g., computer, tablet, smart phone, to name just a few; see also the discussion below with respect to FIG. 6) capable of performing the operations described herein above with respect to determining the aiming direction and initial ball speed for a particular putt. As shown, pendulum putter apparatus 400 and putting diagnostic tool 525 are utilized by individual 520 on golf green 505 having golf cup 515. In this way, individual 520 has access to the results/outputs 550 computed by putting diagnostic tool 525 (as detailed above) by observation via display 555 or over communications link 560 (e.g., any type of communication link for exchanging signals and/or data between devices such as Ethernet, Wi-Fi, and Bluetooth®, to name just a few) and received by portable device 565 (e.g., smart phone) and/or directly by pendulum putter apparatus 400 (as configured with such well-known communications capabilities, but not shown in FIG. 5) that may be utilized in a well-known manner. In this way, in a further embodiment, the execution and completion of putts by golf putting system 500 may be fully automated without the need for significant human intervention.

Illustratively, individual 520 will execute any number of putts using results/output 550 by employing positions 535 and 540, respectively, in terms of setting adjustable putter head 410 at an initial position (i.e., position 535) and releasing adjustable putter head 410 so as to strike (at position 540) golf ball 510 along a specific trajectory (i.e., trajectory 545-1, 545-2 through 545-N), as detailed above, sending golf ball 510 towards golf cup 515. As noted above, in the embodiment, laser 445 is removed after the targeting is completed (i.e., establishing an initial orientation of putter head 410 in the horizontal plane) and before putter head 410 is drawn back to strike golf ball 510. In accordance with an embodiment, as detailed above, one of the trajectories (e.g., trajectory 545-1) has been ranked as the most probable trajectory for successfully completing/making the putt.

Figure 6:
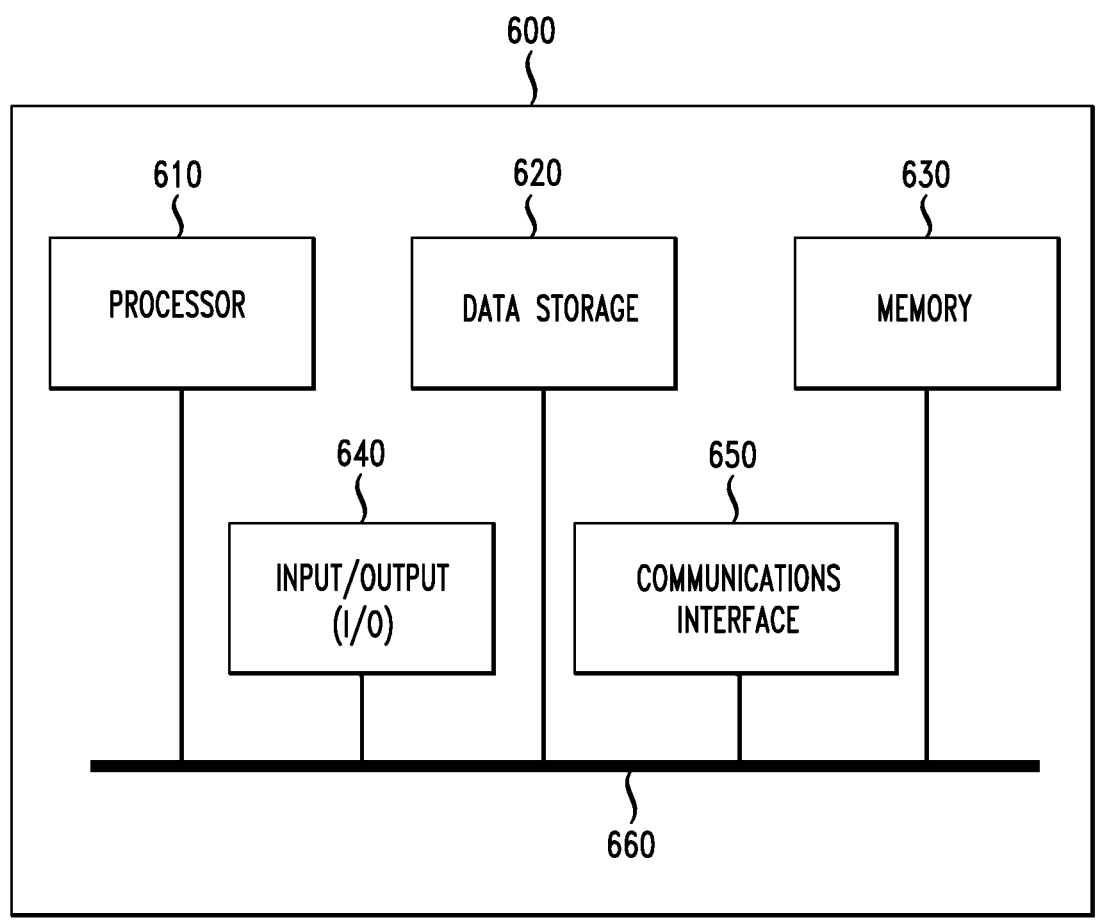
FIG. 6 is a high-level block diagram of an exemplary computer in accordance with an embodiment.

As detailed above, the various embodiments herein can be embodied in the form of methods and apparatuses for practicing those methods. The disclosed methods may be performed by a combination of hardware, software, firmware, middleware, and computer-readable medium (collectively "computer") installed in and/or communicatively connected to a user apparatus. FIG. 6 is a high-level block diagram of an exemplary computer 600 that may be used for implementing a method for determining and simulating a precise putting stroke in accordance with the various embodiments herein. Computer 600 comprises a processor 610 operatively coupled to a data storage device 620 and a memory 630. Processor 610 controls the overall operation of computer 600 by executing computer program instructions that define such operations. Communications bus 660 facilitates the coupling and communication between the various components of computer 600. The computer program instructions may be stored in data storage device 620, or a non-transitory computer readable medium, and loaded into memory 630 when execution of the computer program instructions is desired. Thus, the steps of the disclosed method (see, e.g., FIG. 2 and the associated discussion herein above) can be defined by the computer program instructions stored in memory 630 and/or data storage device 620 and controlled by processor 610 executing the computer program instructions. For example, the computer program instructions can be implemented as computer executable code programmed by one skilled in the art to perform the illustrative operations defined by the disclosed method. Accordingly, by executing the computer program instructions, processor 610 executes an algorithm defined by the disclosed method. Computer 600 also includes one or more communication interfaces 650 for communicating with other devices via a network (e.g., a wireless communications network) or communications protocol (e.g., Bluetooth®). For example, such communication interfaces may be a receiver, transceiver or modem for exchanging wired or wireless communications in any number of well-known fashions. Computer 600 also includes one or more input/output devices 640 that enable user interaction with computer 600 (e.g., camera, display, keyboard, mouse, speakers, microphone, buttons, etc.).

Processor 610 may include both general and special purpose microprocessors, and may be the sole processor or one of multiple processors of computer 600. Processor 610 may comprise one or more central processing units (CPUs), for example. Processor 610, data storage device 620, and/or memory 630 may include, be supplemented by, or incorporated in, one or more application-specific integrated circuits (ASICs) and/or one or more field programmable gate arrays (FPGAs).

Data storage device 620 and memory 630 each comprise a tangible non-transitory computer readable storage medium. Data storage device 620, and memory 630, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 640 may include peripherals, such as a camera, printer, scanner, display screen, etc. For example, input/output devices 640 may include a display device such as a cathode ray tube (CRT), plasma or liquid crystal display (LCD) monitor for displaying information to the user, a keyboard, and a pointing device such as a mouse or a trackball by which the user can provide input to computer 600.

In accordance with various embodiments, a method and apparatus is provided that determines and simulates the proper putting stroke using at least aiming direction and speed for successfully making a particular putt based on particular putting green characteristics and the location of the golf hole on the putting green, and which is interactive with the user thereby providing an enhanced playing experience.

More particularly, in accordance with an embodiment, a library of putting information is compiled using the aforementioned pendulum putter apparatus and putting diagnostic tool wherein the putting information includes the approximate vertical angle necessary for a golf putter to be drawn back to exert the amount of force needed to roll the golf ball the required distance on the golf green using a pendulum motion. In turn, the compiled library of putting information can be used to customize a particular putting experience for a user (e.g., golfer).

Figure 7:
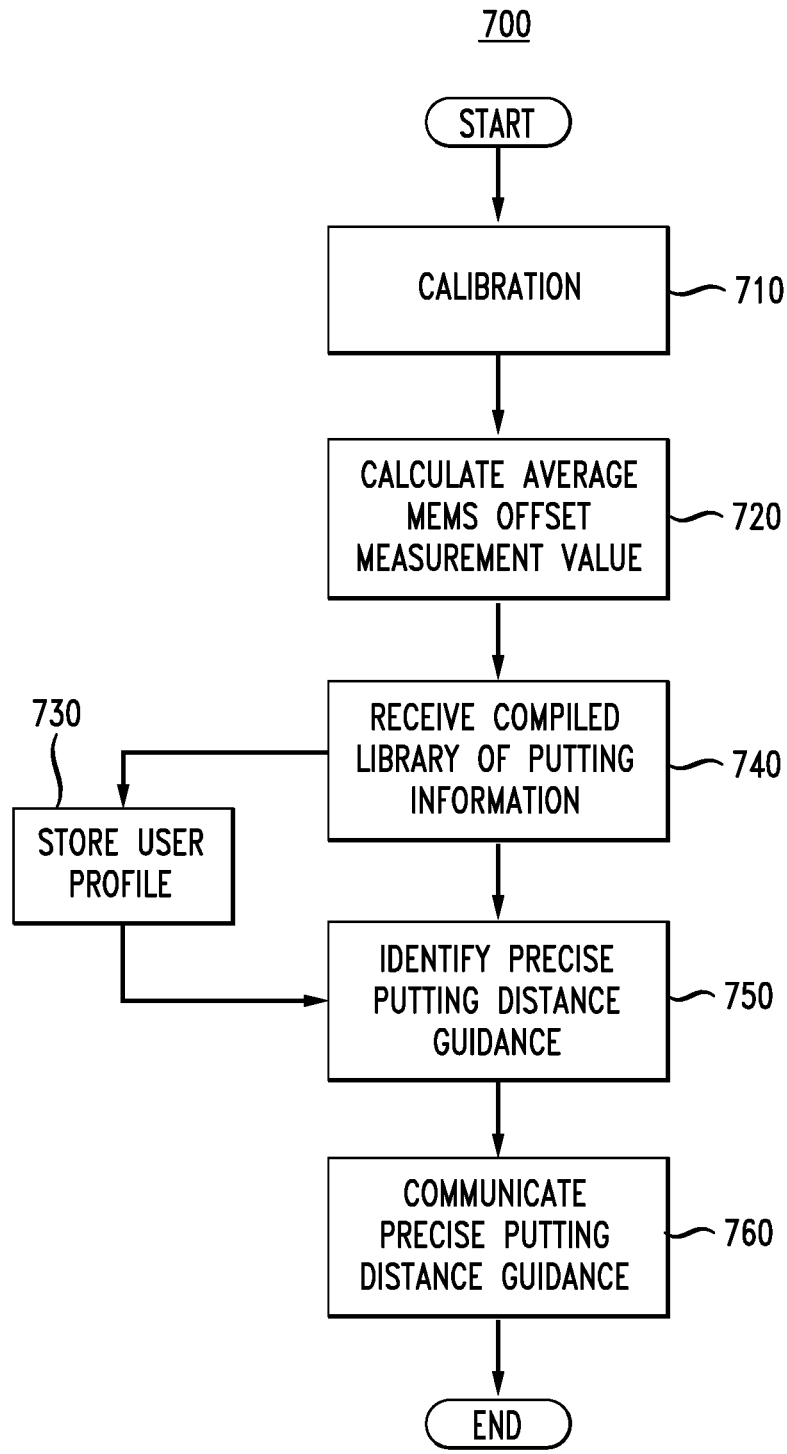
FIG. 7 shows a flowchart of illustrative operations for determining and simulating a precise putting stroke using a mobile device in accordance with an embodiment.

FIG. 7 shows a flowchart of illustrative operations 700 for determining and simulating a precise putting stroke using a mobile device in accordance with an embodiment. Illustratively, the golfer will utilize a mobile device (e.g., smartphone) for initiating operations (e.g., through the execution of a mobile application). At step 710, a calibration process is initiated and execute involving the player attempting a set number of putts (e.g., 10 putts) at a specified distance and green speed, and for each putt, capture and calculate certain mobile device operational information (e.g., information from the MEMS components integrated in the mobile device) at the time of each putt and associated the putting stroke applied by the player. At step 720, the calculation of an average value, for the player, for a plurality of MEMS offset measurements is made. An optional user profile may be created and stored, at step 730, which may store the results of the MEMS offset calculation from step 720. Next, at step 740, the compiled library of putting information is received and, at step 750, a comparison is made between the calculated average player value with that of the compiled library of putting information for the same putt distance and same green speed to identify a set of precise putting distance guidance (e.g., a tempo and a vertical angle needed to make the putt at the specific distance, in other words, a representative putting stroke). That is, the putting stroke defined by the compiled library of putting information (i.e., the simulated putting stroke) is compared with the representative putting stroke of the golfer. In this way, the representative putting stroke is adjusted using the simulated putting stroke in order to identify an adjusted representative putting stroke that is more likely to successfully make the desired putt. At step 760, using a feedback mechanism (e.g., haptic feedback resident on the mobile device, as detailed herein) the set of precise putting distance guidance is communicated (i.e., the adjusted representative putting stroke) to the player in order for the player to apply a putting stroke to make the putt successfully.

Figure 8:
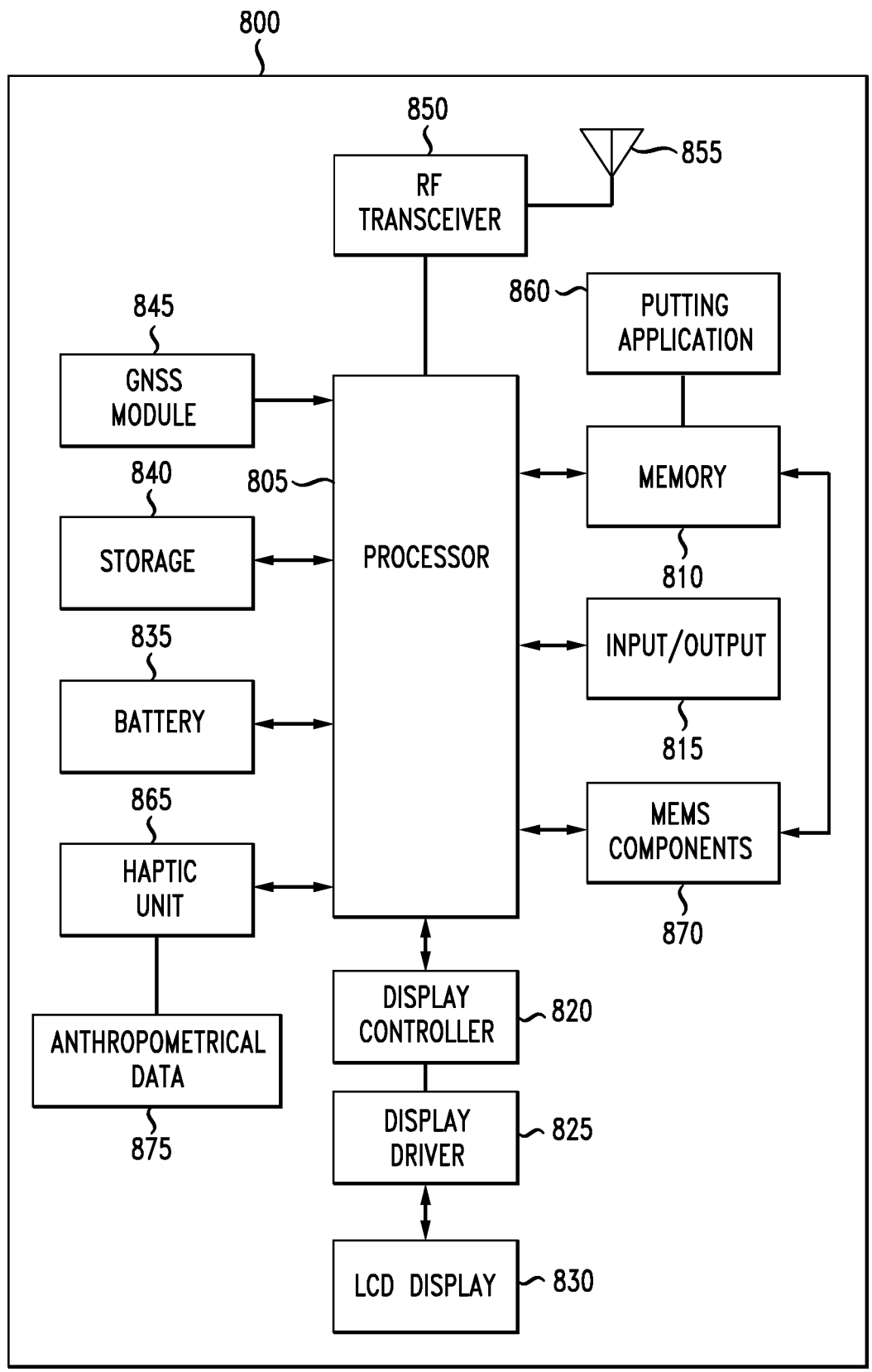
FIG. 8 is a high-level block diagram of an exemplary mobile device for executing the operations of FIG. 7 in accordance with an embodiment.

FIG. 8 is a high-level block diagram of an exemplary mobile device 800 for executing the operations of FIG. 7 in accordance with an embodiment As shown, mobile device 800 (e.g., a smartphone, mobile phone, smart watches, rangefinder, to name just a few) includes processor 805 for controlling the overall operation of mobile device 800, antenna 855, radio frequency (RF) transceiver 850, and GNSS module 845 for receiving and transmitting information, from and to a variety of communications networks, in a conventional and well-known manner. Such information (e.g., data) may also be stored in data storage device 840 and/or memory 810 which each may comprise a tangible non-transitory computer readable storage medium, and/or include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

In accordance with an embodiment, memory 810 also stores putting application 860 for execution by processor 805 which will integrate the operations of mobile device 800 in delivering the interactive putting experience to the user as detailed herein using haptic unit 865. MEMS components 870 deliver conventional MEMS functionality and are utilized to record and collected certain MEMS information for the purposes of deriving mobile device operational information from mobile device 800 as further detailed below.

Mobile device 800 further includes input/output devices 815 which may include peripherals, such as a camera, printer, smart watch, scanner, display screen, virtual reality (VR) display, assisted reality (AR) display, etc. In the illustrative embodiment shown in FIG. 8, display controller 820 operates in conjunction with display driver 825 to display information on LCD display 830 to the user of mobile device 800. Battery 835 (e.g., lithium-ion) provides the overall power supply to mobile device 800 in a well-known fashion.

Figure 9:
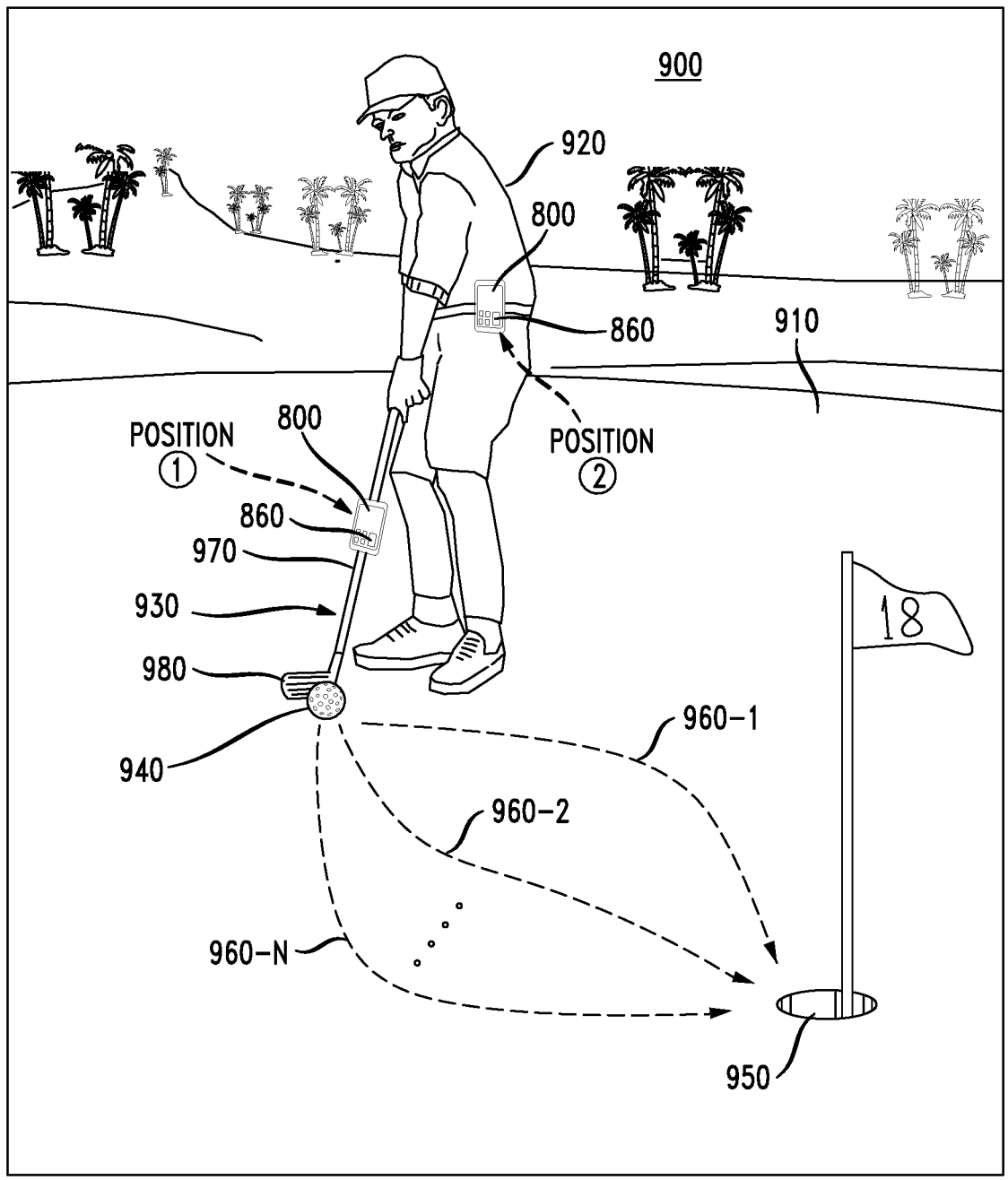
FIG. 9 shows an explanatory diagram of a golf player executing a precise putting stroke using the mobile device of FIG. 8 in accordance with an embodiment.

FIG. 9 shows an explanatory diagram 900 of golfer 920 executing a precise putting stroke on golf green 910 using mobile device 800 in accordance with an embodiment. In accordance with the embodiment, golfer 920 initiates a calibration process using mobile device 800 and putting application 860, as detailed above. Illustratively, mobile device 800 is affixed temporarily (at a first position) to shaft 970 of putter 930 using a conventional clip or other suitable fastener (not shown). In this way, the execution of putting application 860 will initiate a procedure involving golfer 920 attempting a set number of putts (e.g., 10 putts) at a specified distance and green speed associated golf green 910, and for each putt, capture and calculate certain mobile device operational information from mobile device 800 (e.g., information from MEMS components 870 integrated in mobile device 800) at the time of each putt (e.g., putt 960-1, 960-2 through 960-N) and associated the putting stroke applied by golfer 920 to golf ball 940 in an effort to hole the putt in golf hole 950. In accordance with an embodiment, the information recorded by and collected from MEMS components 870 includes at least (i) the angle of the swing plane applied to putter 930; (ii) the starting angle and the finishing angle of putter 930 as defined by putter head 980; and (iii) the final overall swing plane formed using putter head 980 in completing a putting stroke. In an embodiment, putting application 860 will calculate an initial putting trajectory (i.e., line) and distance in order to hole the putt and for the execution of putt 960-1, 960-2 through 960-N by golfer 920.

Thereafter, putting application 860 will perform the calculation of an average value, for golfer 920, for a plurality of MEMS offset measurements, as detailed above. Essentially, using the MEMS offset measurements, a particular putting stroke is defined for golfer 920 (e.g., the ten foot putting stroke of golfer 920 or the five foot putting stroke of golfer 920). Mobile device 800 (and putting application 860) will then access (e.g., either by accessing memory 810 or receiving the information in real-time via input/output 815 across a wireless communication link in a conventional manner). A comparison is made, using putting application 860, between the calculated average player value (e.g., the 10 foot putting stroke of golfer 920) with that of the compiled library of putting information for the same putt distance (e.g., ten feet) and same green speed to identify a set of precise putting distance guidance (e.g., a tempo and a vertical angle needed to make the putt at the specific distance). In the way, in accordance with the embodiment, the recorded putting stroke of golfer 920 (e.g., the ten foot putting stroke) is adjusted, as needed, using the compiled library of putting information to potentially increase the overall accuracy of the putting stroke applied by golfer 920.

In accordance with an embodiment, using a feedback mechanism (e.g., haptic unit 865 on mobile device 800) the set of precise putting distance guidance is communicated to the player in order for the player to apply a putting stroke to make the putt successfully. More particularly, mobile device 800 will use the set of precise putting distance guidance to generate a haptic file including certain haptic data associated with the putting distance guidance and golfer 920. The use of haptics is generally well-known to those of ordinary skill in the art, so this disclosure will not describe these known aspects in any great detail herein. In an embodiment, mobile device 800 is a body sensor (MEMS) mobile phone which works in tandem with a another mobile device 800 which is a wrist (MEMS) smart watch attached to the wrist of golfer 920 such that the tandem of mobile devices capture both upper and lower body measurements to enhance the overall haptic experience. Using the haptic data file (e.g., as stored in memory 810), processor 805 communicates the haptic data file to haptic unit 865. The haptic emulator unit 865 processes the haptic data to produce a haptic, tactile sensation for golfer 920 in order to facilitate an improved tempo, distance control/range, and customize the putting experience to provide golfer 920 with the best possible results. In accordance with the embodiment, mobile device 800 is next affixed (i.e., having been removed from the temporary position (i.e., shown as position 1) on the putter shaft as detailed above for calibration purposes) to the body of golfer 930 at a second position (e.g., on a belt—shown as position 2) using a suitable clip or other conventional device for carrying a mobile device on an individual's body, and the haptic feedback communicates the adjusted putting stroke (as detailed above) to promote a putting stroke that is more likely to succeed in making the putt. Haptic unit 865 thus reproduces the "touch and feel" of the putt using haptic feedback, allowing the user to sense tempo, putter force, and other haptic effects.

In accordance with a further embodiment the putting experience may be highly personalized through haptic unit 865. Before haptic emulator unit 865 renders the haptic data in the haptic file, mobile device 800 may retrieve the user's (e.g., golfer 920) personalized anthropometrical data 875. The anthropometrical data describes the physical, two-dimensional or three-dimensional measurements of the user's various body parts, for example, and this may dimensionally describe the user's hand, arm, head, leg, and/or torso. The anthropometrical data may even dimensionally describe the user's whole body, including weight, height, and body mass, and any other features desirable in playing golf. Whatever the anthropometrical data, mobile device 800 retrieves the user's personalized anthropometrical data (e.g., from memory 810), and mobile device 800 may then process the haptic data in the haptic file using the user's personalized anthropometrical data 875. In this way, haptic unit 865 may be caused to render the haptic data according to the user's personalized anthropometrical data. That is, the haptic unit 865 reproduces the "touch and feel" of the putt (e.g., the putting stroke), but the haptic (and tactile) effect is personalized to the golfer's personal dimensions including any dimensions or other features of putter 930 that golfer 920 is using at the time.

Figure 10:
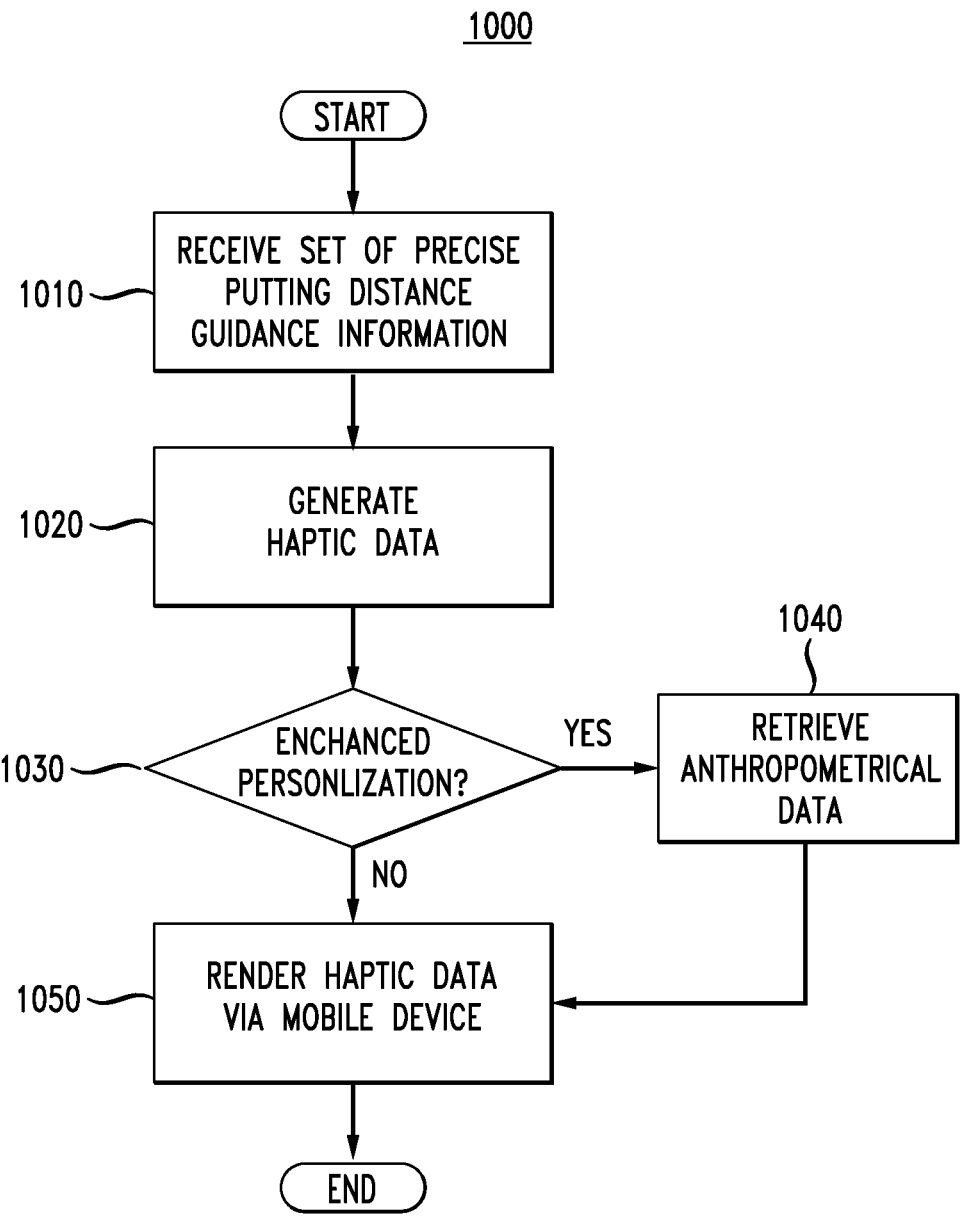
FIG. 10 shows a flowchart of illustrative operations for generating a haptic emulation using the mobile device of FIG. 8 in accordance with an embodiment.

FIG. 10 shows a flowchart of illustrative operations 1000 for generating a haptic rendering and experience using the mobile device of FIG. 8 in accordance with an embodiment. At step 1010, the set of precise putting distance guidance information is received, and at step 1020 the haptic data is generated and, illustratively stored. If further personalization of the putting experience is desired, at step 1030, then the personized anthropometrical data is retrieved at step 1040 to supplement the generated haptic data. The haptic data is then rendered via the mobile device, at step 1050, to golfer 920 as detailed above.

Of course, the experience of golfer 920, produced in accordance with the discussion herein above, may take shape in a variety of ways and circumstances. For example, golfer 920 may align the putt as specified by mobile device 800 and address golf ball 940 with putter 930 and perform one or more practice strokes (i.e., not actually striking golf ball 940 and, for example, making the strokes adjacent to the location of golf ball 940 on golf green 910). Then, mobile device 800, will initiate a short countdown signaling to golfer 920 that the actual putting session is ready to start in accordance with the operations detailed above. For example, golfer 920 may receive a two pulse haptic feedback to begin the back swing of putter 930, and at the apex of the golf stroke (i.e., the vertical angle need to successfully hole/make the putt as determined in accordance with the operation previously described), golfer 920 will receive three (3) short/quick haptic pulses from mobile device 800. At the bottom of the putting stroke (i.e., when impact between putter 930 and golf ball 940 is expected), golfer 920 may receive two (2) short/quick haptic pulses to indicate that golfer 920 should complete the putt by striking golf ball 940 and following through with putter 930 as is done typically in completing a putting stroke. In this way, the tempo and vertical angle needed to make the putt is haptically communicated to golfer 920 to execute the putt with putter 930.

Of course, once golfer 920 has experienced the putting session employing the haptic feedback mechanism of mobile device 800, he may wish to alternate between using mobile device 800 and not using mobile device 800 to practice putting. That is, after utilizing mobile device 800, golfer 920 may wish to rely on muscle memory from executing the prior putting strokes (as haptically assisted) to make further unassisted putts thereby improving the golfer's overall putting stroke and taking such improvement out to the golf course for an actual golf round.

Figure 11A:
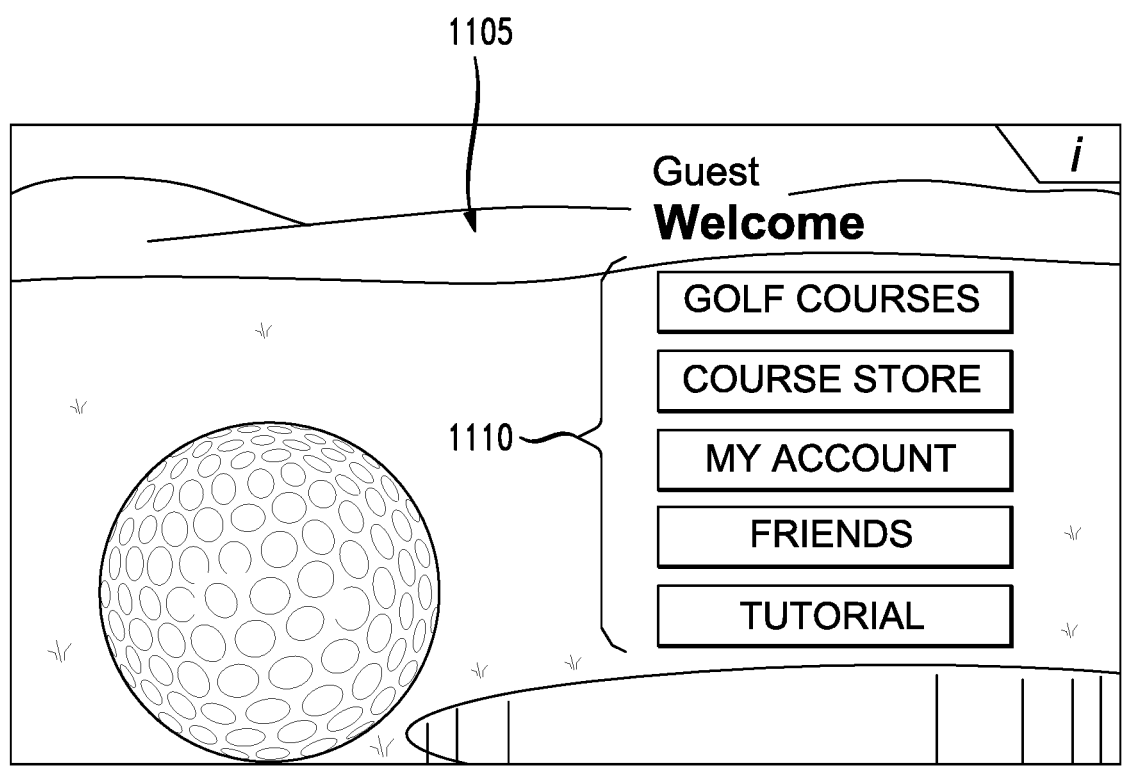
FIGS. 11A-E show exemplary displays and outputs of mobile device 800 in the execution of the illustrative operations of FIGS. 9 and 10.
Figure 11B:
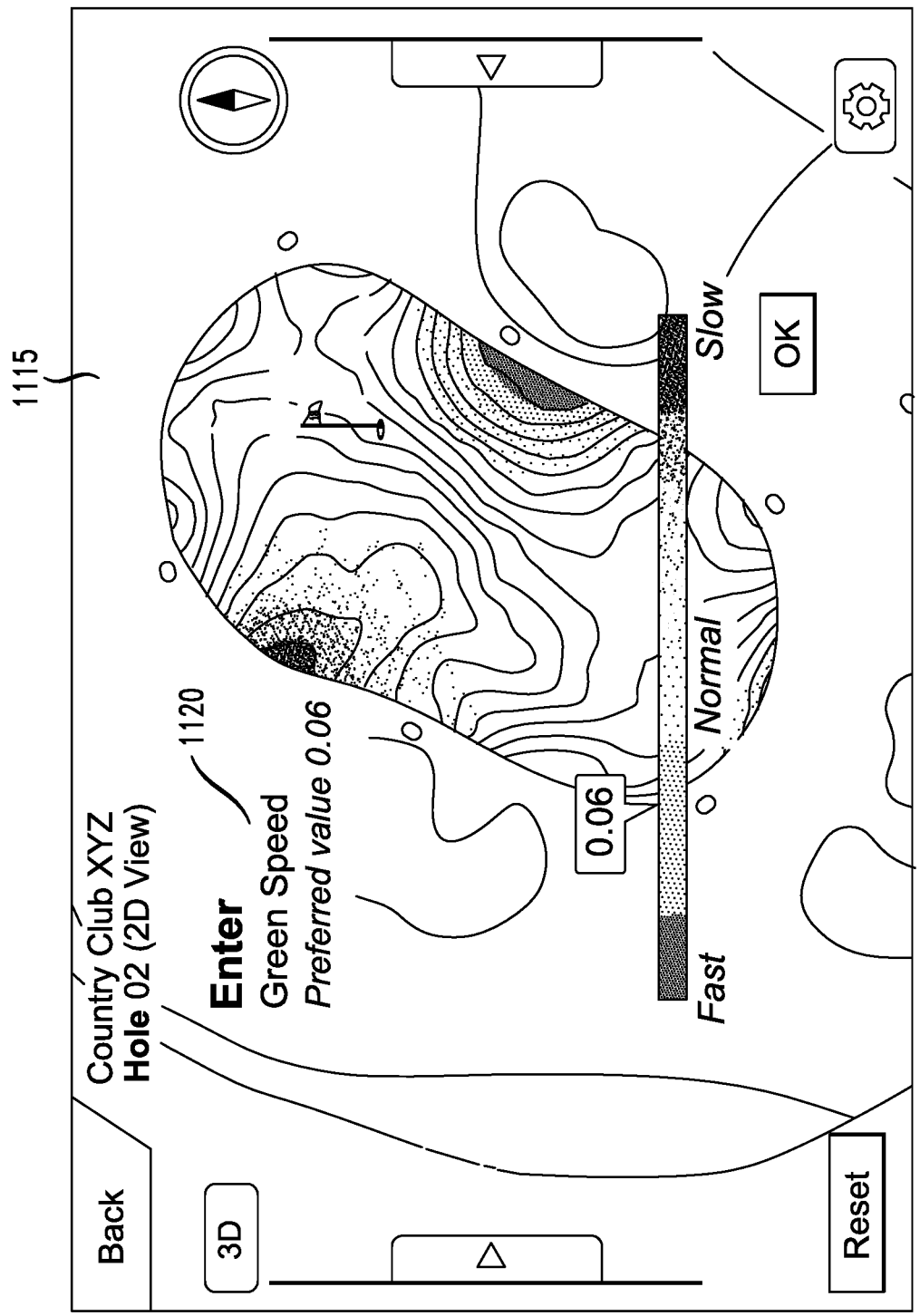
Figure 11C:
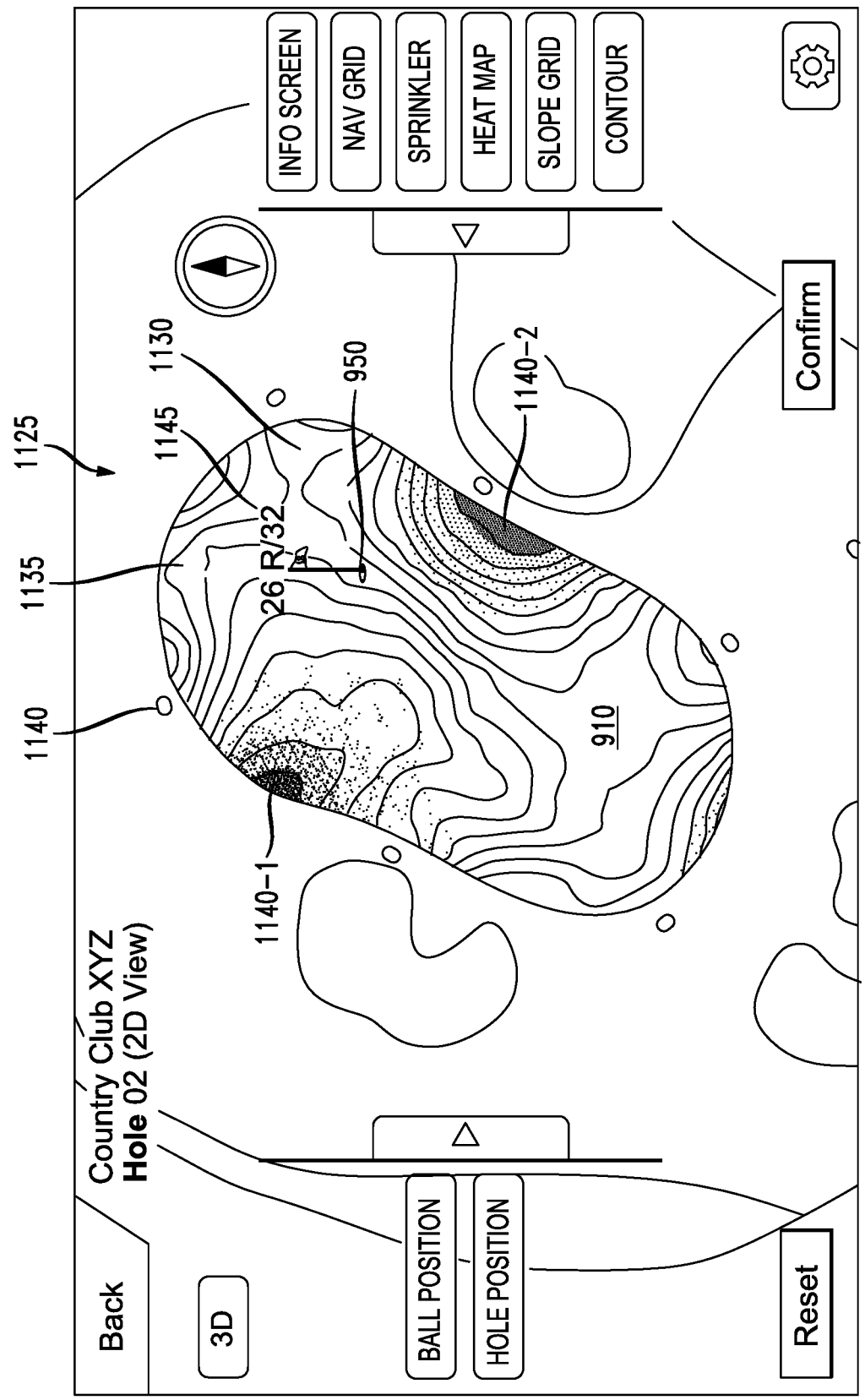

FIGS. 11A-E show exemplary displays and outputs of mobile device 800, in accordance with an embodiment, in the execution of the illustrative operations of FIGS. 9 and 10. In particular, FIG. 11A shows display 1105 which is a welcome display for the user of the mobile application, for example, executing on mobile device 800. The user (e.g., golfer 920) may select various inputs 1110 (e.g., select the desired golf course, store a particular golf course in the device, access a user account, access a list of friends/contacts, and/or run a tutorial of the mobile application). FIG. 11B shows display 1115 which is an input screen for golfer 920 to enter in the relevant green speed 1120 (i.e., Stimpmeter reading) for greens on the golf course that golfer 920 is currently playing for use as detailed above in determining the precise putting guidance. FIG. 11C shows display 1125 which provides a visual display of green 910 and golf hole 950 (as discussed previously and shown in FIG. 9) overlaid with heat map 1130 (i.e., a contour map also showing elevation changes 1140-1 and 1140-2), sprinklers 1140, and contour lines 1135. In addition, hole location 1145 shows the current location of golf hole 950 on golf green 910 together with the aforementioned characteristics.

Figure 11D:
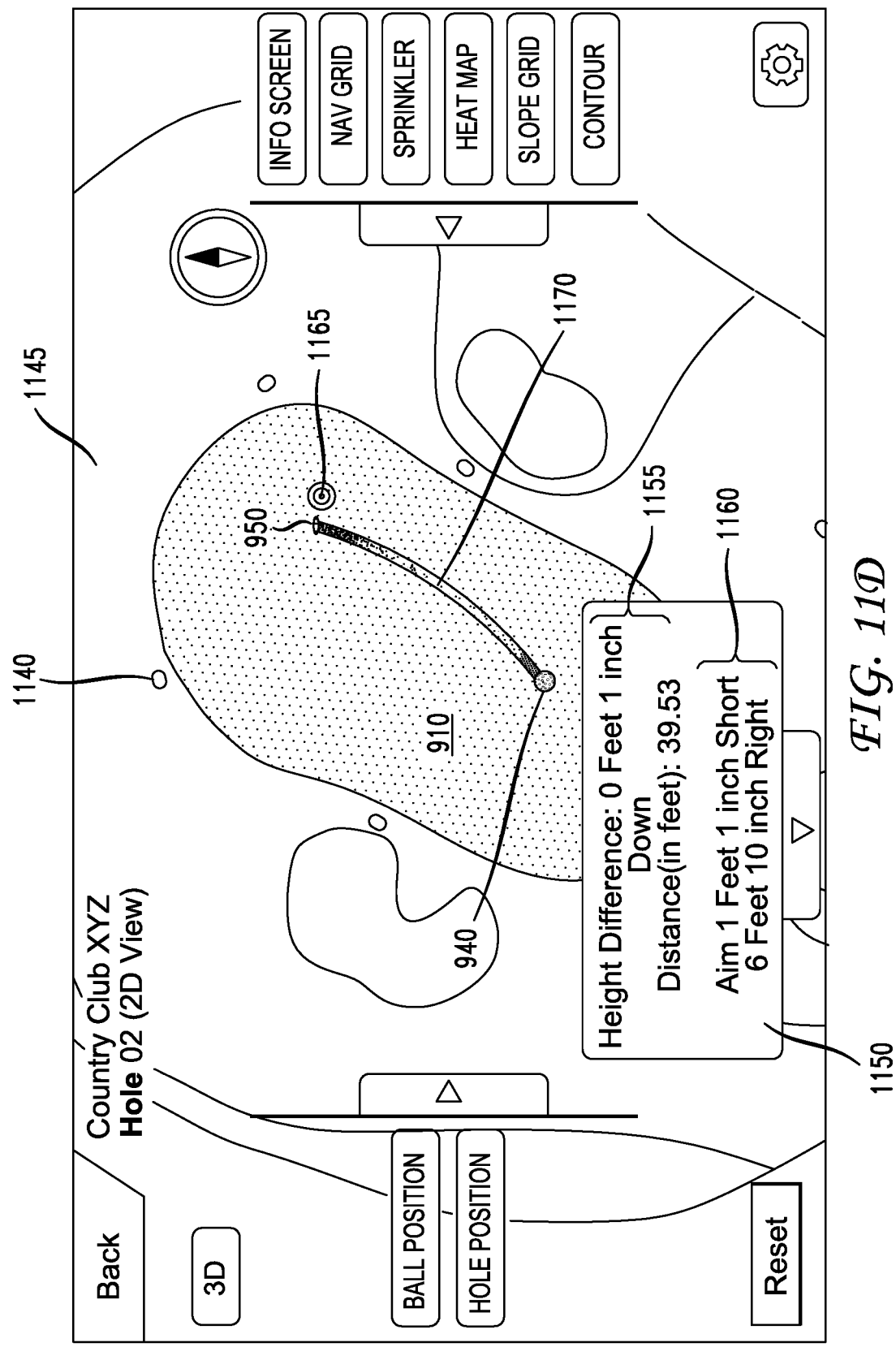
Figure 11E:
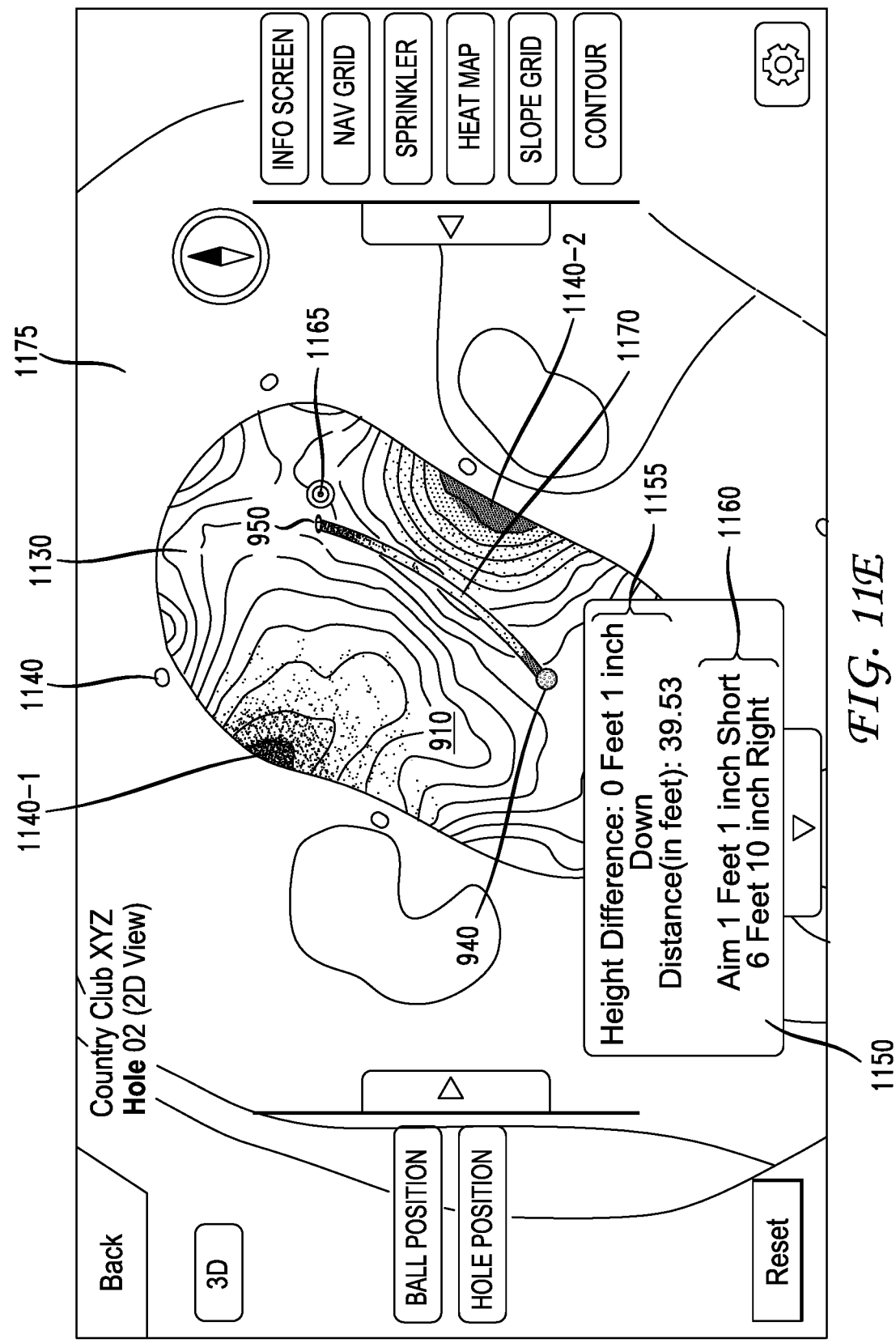

FIG. 11D shows display 1145 with the exemplary results of executing the operations discussed above for determining precise putting information. In particular, display box 1150 shows the specific putt characteristics 1155 to be undertaken in terms of the height difference between golf ball 940 and golf hole 950, and overall distance, and putt characteristics 1160 are the precise aiming characteristics as determined in accordance with the operations detailed previously for golfer 920 to use in making the putt (i.e., hit the putt according to putt characteristics 1160 at target area 1165 along putt trajectory 1170 aided by the haptic feedback provided to golfer 920 via mobile device 800 as detailed above. FIG. 11E shows display 1175 substantially the same information as in FIG. 11D but includes heat map 1130 overlaid onto the display for additional information.

It should be noted that for clarity of explanation, the illustrative embodiments described herein may be presented as comprising individual functional blocks or combinations of functional blocks. The functions these blocks represent may be provided through the use of either dedicated or shared hardware, including, but not limited to, hardware capable of executing software. Illustrative embodiments may comprise digital signal processor ("DSP") hardware and/or software performing the operation described herein. Thus, for example, it will be appreciated by those skilled in the art that the block diagrams herein represent conceptual views of illustrative functions, operations and/or circuitry of the principles described in the various embodiments herein. Similarly, it will be appreciated that any flowcharts, flow diagrams, state transition diagrams, pseudo code, program code and the like represent various processes which may be substantially represented in computer readable medium and so executed by a computer, machine or processor, whether or not such computer, machine or processor is explicitly shown. One skilled in the art will recognize that an implementation of an actual computer or computer system may have other structures and may contain other components as well, and that a high level representation of some of the components of such a computer is for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   receiving a library of putting information for executing a putt of a golf ball to a golf hole located on a golf green, the library comprising at least a plurality of simulated putting strokes, each simulated putting stroke associated with a respective use of a golf putter for executing the putt of the golf ball to the golf hole;
   compiling a set of golfer putting data, the set of golfer putting data including (i) a green speed associated with the golf green; and (ii) data specific to a plurality of actual putting strokes performed by a golfer using the golf putter for executing the putt of the golf ball to the golf hole;
   determining, using the set of golfer putting data compiled, a representative putting stroke for the golfer associated with the putt;
   comparing the plurality of simulated putting strokes to the plurality of actual putting strokes and determining a putting stroke offset;
   adjusting the representative putting stroke using the putting stroke offset;
   communicating the adjusted representative putting stroke to the golfer by rendering, via a user device, haptic sensations to the golfer using a set of haptic data corresponding to the executing of the putt of the golf ball by the golfer; and
   wherein the haptic sensations comprise (i) tactile feedback to begin a backswing of the adjusted representative putting stroke, (ii) tactile feedback at an apex of the adjusted representative putting stroke, and (iii) tactile feedback at a bottom of the adjusted representative putting stroke prior to striking the golf ball to facilitate control of a tempo and a vertical angle of the executing of the putt of the golf ball by the golfer.

2. The method of claim 1, wherein the compiling the set of golfer putting data further comprises:
collecting a set of micro electrical mechanical system (MEMS) data from the user device during the executing the putt of the golf ball by the golfer.

3. The method of claim 2 further comprising:
calculating an average value of a plurality of MEMS offset measurements from the set of MEMS data collected.

4. The method of claim 2 further comprising:
generating the set of haptic data from the set of MEMS data.

5. The method of claim 4 further comprising:
receiving a set of anthropometrical data associated with the golfer, and using the set of anthropometrical data in the rendering of the haptic sensations.

6. The method of claim 2 wherein the set of MEMS data includes (i) an angle of a swing plane applied to the golf putter; (ii) a starting angle and a finishing angle of the golf putter as defined by a putter head of the golf putter; and (iii) an overall swing plane formed using the putter head in completing a particular one of the actual putting strokes performed by the golfer.

7. The method claim 2 wherein the library of putting information is determined by:
receiving a set of inputs, the set of inputs including at least a three-dimensional (3D) surface model associated with the golf green, a first location of the golf hole on the golf green, the first location of the golf hole specified by a first set of 3D geodetic coordinates associated with the 3D surface model, a second location of the golf ball on the golf green, the second location of the golf ball specified by a second set of 3D geodetic coordinates associated with the 3D surface model, and the green speed associated with the golf green;
transforming, using the set of inputs, (i) the first set of 3D geodetic coordinates into a first set of two-dimensional (2D) coordinates, and (ii) the second set of 3D geodetic coordinates into a second set of 2D coordinates, the first set of 2D coordinates and the second set of 2D coordinates being associated with a local coordinate system for the golf green;
performing, using the set of inputs, a calibration specific to the golf putter to identify a set of putter calibration parameters;
determining, using the set of inputs, a search space, the search space including a 2D space comprised of an initial speed of the golf ball and a direction for a plurality of putt trajectories;
simulating, using the set of putter calibration parameters and the 2D space, a plurality of putting strokes, each simulated putting stroke associated with a respective use of the golf putter for executing the putt of the golf ball to the golf hole; and
determining, from the simulation of the plurality of putting strokes, a probability for each of the simulated putting strokes as to whether the respective simulated putting strokes will be successful in the executing of the putt of the golf ball to the golf hole.

8. The method of claim 7 wherein the simulating the plurality of putting strokes further comprises:
specifying a trajectory for each putting stroke of the plurality of putting strokes using at least the initial speed of the golf ball, the green speed, and the 3D surface model.

9. The method of claim 1, wherein the tactile feedback comprises one or more pulses generated by the user device.

10. A device comprising:
a processor;
a haptic unit; and
a memory, for storing computer program instructions, which when executed by the processor, cause the processor to perform operations comprising:
receiving a library of putting information for executing a putt of a golf ball to a golf hole located on a golf green, the library comprising at least a plurality of simulated putting strokes, each simulated putting stroke associated with a respective use of a golf putter for executing the putt of the golf ball to the golf hole;
compiling a set of golfer putting data, the set of golfer putting data including (i) a green speed associated with the golf green; and (ii) data specific to a plurality of actual putting strokes performed by a golfer using the golf putter for executing the putt of the golf ball to the golf hole;
determining, using the set of golfer putting data compiled, a representative putting stroke for the golfer associated with the putt;
comparing the plurality of simulated putting strokes to the plurality of actual putting strokes and determining a putting stroke offset;
adjusting the representative putting stroke using the putting stroke offset;
communicating the adjusted representative putting stroke to the golfer by rendering, in cooperation with the haptic unit, haptic sensations to the golfer using a set of haptic data corresponding to the executing of the putt of the golf ball by the golfer; and
wherein the haptic sensations comprise (i) tactile feedback to begin a backswing of the adjusted representative putting stroke, (ii) tactile feedback at an apex of the adjusted representative putting stroke, and (iii) tactile feedback at a bottom of the adjusted representative putting stroke prior to striking the golf ball to facilitate control of a tempo and a vertical angle of the executing of the putt of the golf ball by the golfer.

11. The device of claim 10 further comprising:
a micro electrical mechanical system (MEMS) device for collecting a set of MEMS data from the device during the executing the putt of the golf ball by the golfer.

12. The device of claim 11 wherein the operations further comprise:
calculating an average value of a plurality of MEMS offset measurements from the set of MEMS data collected.

13. The device of claim 11 wherein the operations further comprise:
generating the set of haptic data from the set of MEMS data.

14. The device of claim 13 wherein the set of MEMS data includes (i) an angle of a swing plane applied to the golf putter; (ii) a starting angle and a finishing angle of the golf putter as defined by a putter head of the golf putter; and (iii) an overall swing plane formed using the putter head in completing a particular one of the actual putting strokes performed by the golfer.

15. The device of claim 13 wherein the operations further comprise:
receiving a set of anthropometrical data associated with the golfer, and using the set of anthropometrical data in the rendering of the haptic sensations.

16. The device of claim 15 further comprising:
a display for displaying a trajectory of the putt associated with the haptic sensations rendered to the golfer in communicating the representative putting stroke adjusted.

17. The device of claim 11 wherein the library of putting information is determined by:
receiving a set of inputs, the set of inputs including at least a three-dimensional (3D) surface model associated with the golf green, a first location of the golf hole on the golf green, the first location of the golf hole specified by a first set of 3D geodetic coordinates associated with the 3D surface model, a second location of the golf ball on the golf green, the second location of the golf ball specified by a second set of 3D geodetic coordinates associated with the 3D surface model, and the green speed associated with the golf green;
transforming, using the set of inputs, (i) the first set of 3D geodetic coordinates into a first set of two-dimensional (2D) coordinates, and (ii) the second set of 3D geodetic coordinates into a second set of 2D coordinates, the first set of 2D coordinates and the second set of 2D coordinates being associated with a local coordinate system for the golf green;
performing, using the set of inputs, a calibration specific to a golf putter apparatus to identify a set of putter calibration parameters;
determining, using the set of inputs, a search space, the search space including a 2D space comprised of an initial speed of the golf ball and a direction for a plurality of putt trajectories;
simulating, using the 2D space, a plurality of putting strokes, each simulated putting stroke associated with a respective use of the golf putter for executing the putt of the golf ball to the golf hole; and
determining, from the simulation of the plurality of putting strokes, a probability for each of the simulated putting strokes as to whether the respective simulated putting strokes will be successful in the executing of the putt of the golf ball to the golf hole.

18. The device of claim 11 wherein the device is a smartphone.

19. The device of claim 10, wherein the tactile feedback comprises one or more pulses generated by the haptic unit in cooperation with the processor.

20. A non-transitory computer-readable medium storing computer program instructions for executing a putt of a golf ball, which, when executed on a processor, cause the processor to perform operations comprising:
receiving a library of putting information for executing the putt of the golf ball to a golf hole located on a golf green, the library comprising at least a plurality of simulated putting strokes, each simulated putting stroke associated with a respective use of a golf putter for executing the putt of the golf ball to the golf hole;
compiling a set of golfer putting data, the set of golfer putting data including (i) a green speed associated with the golf green; and (ii) data specific to a plurality of actual putting strokes performed by a golfer using the golf putter for executing the putt of the golf ball to the golf hole;
determining, using the set of golfer putting data compiled, a representative putting stroke for the golfer associated with the putt;
comparing the plurality of simulated putting strokes to the plurality of actual putting strokes and determining a putting stroke offset;
adjusting the representative putting stroke using the putting stroke offset;
communicating the adjusted representative putting stroke to the golfer by rendering, via a user device, haptic sensations to the golfer using a set of haptic data corresponding to the executing of the putt of the golf ball by the golfer; and
wherein the haptic sensations comprise (i) tactile feedback to begin a backswing of the adjusted representative putting stroke, (ii) tactile feedback at an apex of the adjusted representative putting stroke, and (iii) tactile feedback at a bottom of the adjusted representative putting stroke prior to striking the golf ball to facilitate control of a tempo and a vertical angle of the executing of the putt of the golf ball by the golfer.

21. The non-transitory computer-readable medium of claim 20 wherein the compiling the set of golfer putting further comprises:
collecting a set of micro electrical mechanical system (MEMS) data from the user device during the executing the putt of the golf ball by the golfer.

22. The non-transitory computer-readable medium of claim 21 wherein the operations further comprise:
generating the set of haptic data from the set of MEMS data.

23. The non-transitory computer-readable medium of claim 22 wherein the set of MEMS data includes (i) an angle of a swing plane applied to the golf putter; (ii) a starting angle and a finishing angle of the golf putter as defined by a putter head of the golf putter; and (iii) an overall swing plane formed using the putter head in completing a particular one of the actual putting strokes performed by the golfer.

24. The non-transitory computer-readable medium of claim 20, wherein the tactile feedback comprises one or more pulses generated by the user device.

* * * * *